US010583439B2

(12) United States Patent
Koksal et al.

(10) Patent No.: US 10,583,439 B2
(45) Date of Patent: Mar. 10, 2020

(54) HYDRODYNAMIC FOCUSING APPARATUS AND METHODS

(71) Applicant: CYTONOME/ST, LLC, Boston, MA (US)

(72) Inventors: Erin Koksal, Denver, CO (US); Johnathan Charles Sharpe, Hamilton (NZ); Kristopher Scott Buchanan, Fort Collins, CO (US); Blair D. Morad, Ipswich, MA (US)

(73) Assignee: CYTONOME/ST, LLC, Bedford, MA (US)

(*) Notice: Subject to any disclaimer, the term of this patent is extended or adjusted under 35 U.S.C. 154(b) by 673 days.

(21) Appl. No.: 14/213,800

(22) Filed: Mar. 14, 2014

(65) Prior Publication Data
US 2014/0318645 A1 Oct. 30, 2014

Related U.S. Application Data
(60) Provisional application No. 61/785,734, filed on Mar. 14, 2013.

(51) Int. Cl.
B01L 3/00 (2006.01)
B01F 13/00 (2006.01)
(Continued)

(52) U.S. Cl.
CPC .... *B01L 3/502776* (2013.01); *B01F 13/0062* (2013.01); *F17D 1/08* (2013.01);
(Continued)

(58) Field of Classification Search
CPC ....... G01N 2015/1413; B01L 3/502776; B01L 2200/0636; B01F 13/0062; Y10T 137/2076; F16K 2099/008
See application file for complete search history.

(56) References Cited

U.S. PATENT DOCUMENTS 3,649,829 A 3/1972 Randolph
4,126,425 A 11/1978 Twigge-Molecey
(Continued)

FOREIGN PATENT DOCUMENTS

WO 1998043066 A1 10/1998
WO 1999060397 A1 11/1999
(Continued)

OTHER PUBLICATIONS

International Preliminary Report on Patentability issued in International Application No. PCT/US2004/036548, dated May 15, 2006.
(Continued)

*Primary Examiner* — Atif H Chaudry
(74) *Attorney, Agent, or Firm* — McCarter & English, LLP; David R. Burns

(57) ABSTRACT

A microfluidic chip having a micro channel for processing a sample is provided. The micro channel may focus the sample by using focusing fluid and a core stream forming geometry. The core stream forming geometry may include a lateral fluid focusing component and one or more vertical fluid focusing components. A microfluidic chip may include a plurality micro channels operating in parallel on a microfluidic chip.

23 Claims, 20 Drawing Sheets

(51) Int. Cl.
  *G01N 15/14* (2006.01)
  *F16K 99/00* (2006.01)
  *F17D 1/08* (2006.01)
  *F17D 5/00* (2006.01)

(52) U.S. Cl.
  CPC ........... *F17D 5/00* (2013.01); *G01N 15/1404* (2013.01); *B01L 2200/0636* (2013.01); *F16K 2099/008* (2013.01); *G01N 2015/1409* (2013.01); *G01N 2015/1411* (2013.01); *G01N 2015/1413* (2013.01); *Y10T 137/2076* (2015.04); *Y10T 137/8359* (2015.04)

(56) References Cited

U.S. PATENT DOCUMENTS

| | | | |
|---|---|---|---|
| 4,503,385 A | 3/1985 | Haynes | |
| 4,752,131 A | 6/1988 | Eisenlauer et al. | |
| 4,756,427 A | 7/1988 | Gohde et al. | |
| 4,836,039 A | 6/1989 | de Silva et al. | |
| 4,844,610 A | 7/1989 | North, Jr. | |
| 4,954,715 A | 9/1990 | Zold | |
| 4,983,038 A | 1/1991 | Ohki et al. | |
| 5,021,244 A | 6/1991 | Spaulding | |
| 5,030,002 A | 7/1991 | North, Jr. | |
| 5,040,890 A | 8/1991 | North, Jr. | |
| 5,135,759 A | 8/1992 | Johnson | |
| 5,311,290 A | 5/1994 | Olson et al. | |
| 5,521,079 A | 5/1996 | Dorian et al. | |
| 5,808,737 A | 9/1998 | Edens et al. | |
| 5,880,835 A | 3/1999 | Yamazaki et al. | |
| 5,902,745 A | 5/1999 | Butler et al. | |
| 6,053,667 A | 4/2000 | Sakai et al. | |
| 6,159,739 A | 12/2000 | Weigl et al. | |
| 6,365,106 B1 | 4/2002 | Nagai | |
| 6,473,171 B1 | 10/2002 | Buttry et al. | |
| 6,475,364 B1 | 11/2002 | Dubrow et al. | |
| 6,506,609 B1 | 1/2003 | Wada et al. | |
| 6,537,501 B1 | 3/2003 | Holl et al. | |
| 6,576,194 B1 | 6/2003 | Holl et al. | |
| 6,592,821 B1 | 7/2003 | Wada et al. | |
| 6,663,352 B2 | 12/2003 | Sabini et al. | |
| 6,674,525 B2 | 1/2004 | Bardell et al. | |
| 6,710,874 B2 | 3/2004 | Mavliev | |
| 6,749,374 B1 | 6/2004 | Lane et al. | |
| 6,808,075 B2 | 10/2004 | Bohm et al. | |
| 6,877,528 B2 | 4/2005 | Gilbert et al. | |
| 6,890,093 B2 | 5/2005 | Karp et al. | |
| 7,105,355 B2 * | 9/2006 | Kurabayashi | G01N 15/1404 422/73 |
| 7,116,407 B2 | 10/2006 | Hansen et al. | |
| 7,157,274 B2 | 1/2007 | Bohm et al. | |
| 7,195,920 B2 | 3/2007 | Seidel et al. | |
| 7,208,265 B1 | 4/2007 | Schenk | |
| 7,223,371 B2 | 5/2007 | Hayenga et al. | |
| 7,242,474 B2 | 7/2007 | Cox et al. | |
| 7,298,478 B2 | 11/2007 | Gilbert et al. | |
| 7,311,476 B2 | 12/2007 | Gilbert et al. | |
| 7,355,696 B2 | 4/2008 | Mueth et al. | |
| 7,402,131 B2 | 7/2008 | Mueth et al. | |
| 7,419,784 B2 | 9/2008 | Dubrow et al. | |
| 7,434,982 B2 | 10/2008 | Nagasawa et al. | |
| 7,442,339 B2 | 10/2008 | Sundararajan et al. | |
| 7,452,726 B2 | 11/2008 | Chou et al. | |
| 7,492,522 B2 | 2/2009 | Gilbert et al. | |
| 7,553,453 B2 | 6/2009 | Gu et al. | |
| 7,569,788 B2 | 8/2009 | Deshpande et al. | |
| 7,611,309 B2 | 11/2009 | Gilbert et al. | |
| 7,638,339 B2 | 12/2009 | Sundararajan et al. | |
| 7,641,856 B2 | 1/2010 | Padmanabhan et al. | |
| 7,751,040 B2 | 7/2010 | Chang et al. | |
| 7,760,351 B2 | 7/2010 | Cox et al. | |
| 7,772,287 B2 | 8/2010 | Higuchi et al. | |
| 7,776,268 B2 | 8/2010 | Rich | |
| 7,802,686 B2 | 9/2010 | Takagi et al. | |
| 7,833,421 B2 | 11/2010 | Huymann | |
| 7,850,907 B2 | 12/2010 | Sundararajan | |
| 7,993,934 B2 | 8/2011 | Tabata et al. | |
| 7,997,831 B2 | 8/2011 | Gilbert et al. | |
| 8,123,044 B2 | 2/2012 | Johnson et al. | |
| 8,263,387 B2 | 9/2012 | Pagano et al. | |
| 8,277,764 B2 | 10/2012 | Gilbert et al. | |
| 8,383,043 B2 | 2/2013 | Padmanabhan et al. | |
| 8,426,159 B2 | 4/2013 | Balagadde et al. | |
| 8,487,273 B2 | 7/2013 | Ito et al. | |
| 8,528,427 B2 | 9/2013 | Vrane et al. | |
| 8,529,161 B2 | 9/2013 | Gilbert et al. | |
| 8,573,060 B2 | 11/2013 | Huang et al. | |
| 8,651,138 B2 | 2/2014 | Villarruel et al. | |
| 8,695,618 B2 | 4/2014 | Kim et al. | |
| 8,808,642 B2 | 8/2014 | Lim et al. | |
| 8,961,904 B2 | 2/2015 | Xia et al. | |
| 9,446,912 B2 | 9/2016 | Gilbert et al. | |
| 9,486,757 B2 | 11/2016 | Romanowsky et al. | |
| 9,588,100 B2 | 3/2017 | Appleyard et al. | |
| 9,802,767 B2 | 10/2017 | Gilbert et al. | |
| 2002/0097633 A1 | 7/2002 | O'Connor et al. | |
| 2002/0149766 A1 | 10/2002 | Bardell et al. | |
| 2004/0043506 A1 * | 3/2004 | Haussecker | B01J 19/0093 436/180 |
| 2004/0120856 A1 | 6/2004 | Andersson et al. | |
| 2004/0169867 A1 | 9/2004 | Sharpe | |
| 2005/0112541 A1 | 5/2005 | Durack et al. | |
| 2005/0123450 A1 * | 6/2005 | Gilbert | B65G 51/08 422/81 |
| 2006/0113190 A1 | 6/2006 | Kumik | |
| 2007/0014695 A1 | 1/2007 | Yue et al. | |
| 2008/0185057 A1 | 8/2008 | Prakash et al. | |
| 2008/0311005 A1 | 12/2008 | Kim et al. | |
| 2009/0116005 A1 | 5/2009 | Furuki et al. | |
| 2009/0126516 A1 | 5/2009 | Yamamoto et al. | |
| 2009/0178716 A1 | 7/2009 | Kaduchak et al. | |
| 2009/0201504 A1 * | 8/2009 | Ho | B01L 3/502761 356/399 |
| 2011/0003303 A1 | 1/2011 | Pagano et al. | |
| 2011/0008817 A1 | 1/2011 | Durack | |
| 2011/0196637 A1 | 8/2011 | Sharpe et al. | |
| 2012/0009025 A1 | 1/2012 | Gilbert et al. | |
| 2012/0097633 A1 | 4/2012 | Marsollier | |
| 2012/0138152 A1 | 6/2012 | Villarruel et al. | |
| 2012/0196314 A1 | 8/2012 | Nawaz et al. | |
| 2012/0277902 A1 | 11/2012 | Sharpe et al. | |
| 2012/0301883 A1 | 11/2012 | Pagano et al. | |
| 2013/0213488 A1 * | 8/2013 | Weitz | C12M 23/16 137/13 |
| 2013/0334407 A1 | 12/2013 | Perrault, Jr. et al. | |
| 2014/0027356 A1 | 1/2014 | Ito | |
| 2014/0050540 A1 | 2/2014 | Gilbert et al. | |
| 2014/0085898 A1 | 3/2014 | Perrault, Jr. | |
| 2014/0339445 A1 | 11/2014 | Sharpe et al. | |
| 2017/0102381 A1 | 4/2017 | Griffiths et al. | |
| 2018/0208412 A1 | 7/2018 | Gilbert et al. | |

FOREIGN PATENT DOCUMENTS

| | | |
|---|---|---|
| WO | 00/070080 A1 | 11/2000 |
| WO | 2003078972 A1 | 9/2003 |
| WO | 2005/022147 A1 | 3/2005 |
| WO | 2005/042137 A2 | 5/2005 |
| WO | 2011/003073 A1 | 1/2011 |
| WO | 2012/027366 A2 | 3/2012 |
| WO | 2015/009284 A1 | 1/2015 |

OTHER PUBLICATIONS

International Preliminary Report on Patentability issued in International Application No. PCT/US2014/029090, dated Sep. 24, 2015.
International Search Report and Written Opinion issued in International Application No. PCT/US2014/029090, dated Jul. 11, 2014.
International Search Report and Written Opinion issued in International Application No. PCT/US2004/36548, dated Mar. 17, 2006.

(56) References Cited

OTHER PUBLICATIONS

Australian Patent Examination Report No. 1, Patent Appl. No. 2011205167, dated Jul. 6, 2012.
Examination Report Issued in European Application No. 14722885.2 dated Mar. 16, 2017. p. 1-9.
First Examination Report Issued in New Zealand Application No. 711384 dated Jun. 23, 2017. p. 1-4.
First Office Action by State Intellectual Property Office of P.R. China for Chinese Application No. 201480028102.2 dated May 15, 2017.
Altendorf, Eric, et al. "Results obtained using a prototype microfluidics-based hematology analyzer." In Micro Total Analysis Systems 1998: Proceedings of the uTAS '98 Workshop, held in Banff, Canada, Oct. 13-16, 1998 (pp. 73-76). Springer Netherlands. Oct. 1998.
Di Carlo, Dino, and Luke P. Lee. "Enhanced Velocity Gradients within Microfluidics for Cellular Manipulation." In Micro Total Analysis Systems 2002: Proceedings of the uTAS 2002 Symposium, held in Nara, Japan, Nov. 3-7, 2002. vol. 2. (pp. 799-801) Springer Netherlands, Nov. 2002.
Klank, H., Goranovic, G., Kutter, J.P., Gjelstrup, H., Michelsen, J. and Westergaard, C.H.. "PIV measurements in a microfluidic 3D-sheathing structure with three-dimensional flow behaviour." Journal of Micromechanics and Microengineering, 12(6), p. 862, (Oct. 2002).
Miyake, Ryo, et al. "A development of micro sheath flow chamber." Micro Electro Mechanical Systems, MEMS '91, Proceedings. An Investigation of Micro Structures, Sensors, Actuators, Machines and Robots. IEEE. (Jan. 1991). DOI: 10.1109/MEMSYS.1991.114808.
Nieuwenhuis, J. H., Bastemeijer, J., Sarro, P. M., & Vellekoop, M. J. "Virtual Flow Channel: A Novel Microfluidics System with Orthogonal Dynamic Control of Sample Flow Dimensions." In Micro Total Analysis Systems 2002: Proceedings of uTAS 2002 Symposium, held in Nara, Japan, Nov. 3-7, 2002 (pp. 103-105). Springer Science +Business Media Dordrecht. Nov. 3, 2002.
Nieuwenhuis, J. H., Lee, S. S., Bastemeijer, J., & Vellekoop, M. J. "Particle-shape sensing-elements for integrated flow cytometer." In Micro Total Analysis Systems 2001: Proceedings of the uTAS 2001 Symposium, held in Monterey, CA, USA Oct. 21-25, 2001 (pp. 357-358). Springer Netherlands. Oct. 21, 2001.
Nieuwenhuis, Jeroen H., et al. "Integrated flow-cells for novel adjustable sheath flows." Lab on a Chip 3.2 (Mar. 2003): 56-61.
Pinkel, D., and R. Stovel. "Flow chambers and sample handling." in Flow Cytometry: Instrumentation and Data Analysis, (Eds: M. Van Dilla et al.). Academic Press, Inc., Orlando, FL. (1985): pp. 91-99.
Shapiro, Howard M. "Practical flow cytometry." John Wiley and Sons, Hoboken, NJ. 4th Ed. (2003) pp. 55-57, pp. 166-169.
Shapiro, Howard M. "Practical flow cytometry." Wiley-Liss, Inc. 3rd Ed. (1995): pp. 15-17, pp. 133-135.
Sobek, D, Senturia, S.D, and Gray, M.L., "Microfabricated Fused Silica Flow Chambers for Flow Cytometry," Technical Digest of the IEEE Solid State Sensor and Actuator Workshop 1994, Hilton Head Island, SC, Jun. 13-16, 1994, pp. 260-263.
Sobek, D., A. Young, M.L. Gray, and S. Senturia, "A microfabricated flow chamber for optical measurements in fluids." Micro Electro Mechanical Systems, 1993, MEMS '93, Proceedings An Investigation of Micro Structures, Sensors, Actuators, Machines and Systems. IEEE. Feb. 10, 1993.
Sobek, Daniel. "Microfabricated fused silica flow chambers for flow cytometry." Diss. Massachusetts Institute of Technology, Sep. 1996.
Tashiro, K., Sekiguchi, T., Shoji, S., Funatsu, T., Masumoto, W., & Sato, H. "Design and simulation of particles and biomolecules handling micro flow cells with three-dimensional sheath flow." In Micro Total Analysis Systems 2000: Proceedings of the uTAS Symposium, held in Enschede, The Netherlands, May 14-18, 2000 (pp. 209-212). Springer Netherlands. May 14, 2000.
Weigl, Bernhard H., et al. "Design and rapid prototyping of thin-film laminate-based microfluidic devices." Biomedical Microdevices 3.4 (Dec. 2001): 267-274.
Expert Report of Dino Di Carlo, Ph.D., Inguran, LLC d/b/a Stgenetics, XY, LLC, and Cytonome/St, LLC v. ABS Global, Inc., Genus PLC, and Premium Genetics (UK) Ltd. Case No. 17-cv-446. 762 pages, Jul. 23, 2018.
Joint Table of Terms Requiring Construction. Inguran, LLC d/b/a Stgenetics, XY, LLC, and Cytonome/St, LLC, v. ABS Global, Inc., Genus PLC, and Premium Genetics (UK) Ltd., dated Aug. 30, 2018. 8 pages.
Petition for Inter Partes Review. ABS Global, Inc., v. Cytonome/St, LLC, Case No. IPR2017-02097, dated Oct. 5, 2017, 84 pages.
Petition for Inter Partes Review. ABS Global, Inc., v. Cytonome/St, LLC, Case No. IPR2017-02161, dated Oct. 5, 2017, 82 pages.
Petition for Inter Partes Review. ABS Global, Inc., v. Cytonome/St, LLC, Case No. IPR2017-02162, dated Oct. 5, 2017, 87 pages.
Petition for Inter Partes Review. ABS Global, Inc., v. Cytonome/St, LLC, Case No. IPR2017-02163, dated Oct. 5, 2017, 78 pages.
Plaintiffs' Disclusure of Claim Terms and Proposed Constructions. Inguran, LLC d/b/a Stgenetics, XY, LLC and Cytonome/St, LLC v ABS Global, Inc., Genus PLC and Premium Genetics (UK) Ltd. Civil Action No. 17-cv-446. 9 pages, dated Apr. 12, 2018.
Plaintiffs' Original Complaint. Case: 3:17-cv-00446, Inguran, LLC d/b/a Stgenetics, XY, LLC and Cytonome/St, LLC v. ABS Global, Inc., Genus PLC, and Premium Genetics (UK) LTD. Filed Jun. 7, 2017, 36 pages.
Plaintiffs' Responses to Defendants' Identification of Claim Terms and Proposed Constructions. Inguran, LLC d/b/a Stgenetics, XY, LLC and Cytonome/St, LLC v ABS Global, Inc., Genus PLC and Premium Genetics (UK) Ltd. Civil Action No. 17-cv-446. 9 pages, dated May 10, 2018.
Request for Rehearing, ABS Global, Inc. v. Cytonome/ST, LLC, Case No. IPR2017-02161, U.S. Pat. No. 7,611,309. 18 pages, May 9, 2018.
Request for Rehearing, ABS Global, Inc. v. Cytonome/ST, LLC, Case No. IPR2017-02163, U.S. Pat. No. 7,311,476. 14 pages, May 9, 2018.
Revocation Petition before the IPAB in respect of Indian Patent No. 240790. (IPAB Case No.: sr. no. 28/2017/PT/CHN in ORA). Petitioner: ABS Global, Inc., Respondents: 1. Cytonome/St, LLC, 2. The Controller of Patents. May 18, 2017. Includes Supporting Affidavit. 63 pages.
Scheduling Order 37 C.F.R. § 42.5. ABS Global, Inc., v. Cytonome/St, LLC. Case IPR2017-02097, Entered Apr. 17, 2018. 9 pages.
Cytonome/St, LLC's Patent Owner Response. ABS Global, Inc., v. Cytonome/St, LLC. Case IPR2017-02162, U.S. Pat. No. 9,446,912. 70 pages, Aug. 1, 2018.
Cytonome/St, LLC's Patent Owner Response. ABS Global, Inc., v. Cytonome/St, LLC. Case IPR2017-02097, U.S. Pat. No. 8,529,161. 74 pages, Aug. 1, 2018.
Petitioner's Reply, ABS Global, Inc., v. Cytonome/St, LLC. Case IPR2017-02097, U.S. Pat. No. 8,529,161. 32 pages, Oct. 9, 2018.
Petitioner's Reply, ABS Global, Inc., v. Cytonome/St, LLC. Case IPR2017-02162, U.S. Pat. No. 9,446,912. 29 pages, Oct. 9, 2018.
First Amended Joint Table of Terms Requiring Construction. Inguran, LLC d/b/a Stgenetics, XY, LLC, and Cytonome/St, LLC v. ABS Global, Inc., Genus PLC, and Premium Genetics (UK) Ltd., Civil Action No. 17-cv-446. 8 pages, Sep. 19, 2018.
Bousse et al., Novel Injection Schemes for Ultra-high Speed DNA Separations. Micro Total Analysis Systems. A. van den Berg (Ed). Kluwer Academic Press. pp. 415-418, (2000).
Bousse et al., Optimization of Sample Injection Components in Electrokinetic Microfluidic Systems. Twelfth IEEE International Conference on Micro Electro Mechanical Systems. pp. 309-314, Jan. 21, 1999.
Chen et al., Experimental and Numerical Study of Electrokinetic and Pressure Drive Flows in Straight and Curved Micro-Channels. Micro Total Analysis Systems, J.M. Ramsey (Ed.), Kluwer Academic Publishers. pp. 609-610, (2001).
Dean et al., Hydrodynamics Orientation of Sperm Heads for Flow Cytometry. Biophys J. Jul. 1978;23;7-13.
Deshpande et al., CAD Analysis of PCR Well Containment. 2nd International Conference on Modeling and Simulation of Microsystems. pp. 350-354, Apr. 21, 1999.

(56) References Cited

OTHER PUBLICATIONS

Deshpande et al, Numerical Framework for the Modeling of Electrokinetic Flow. SPiE Conference on Microfluidic Devices and Systems. Sep. 1998;3515:217-227.
Deshpande et al., Predictive Design of Reverse Injection Mechanism for Electrokinetic DNA Sample Injection. Solid-State Sensor and Actuator Workshop. pp. 128-133, Jun. 4-8, 2000.
Fulwyler et al., Hydrodynamic Orientation of Cells. The Journal of Histochemistry and Cytochemistry. Feb. 23, 1977;25(7):781-783.
Godin et al., Integrated Fluidic Photonics for Multi-Parameter In-Plane Detection in Microfluidic Flow Cytometry. Conference Proceedings—Lasers and Electro-Optics Society Annual Meeting-LEOS. pp. 605-606, Nov. 2006.
Hara et al., Fabrication of On-chip Sorter Devices with Submicrometer Scale Channels and Self-aligned Microelectrodes. Y. Baba (Ed.), Micro Total Analysis Systems, vol. 1. 2002;124-126.
Johnson et al., Sex preselection: high-speed flow cytometric sorting of X and Y sperm for maximum efficiency. Theriogenology. Dec. 1999;52(8):1323-41.
Klank et al., PIV measurements in a microfluidic 3D-sheathing structure with three-dimensional flow behaviour. J Micromech Microeng. Oct. 3, 2002;12:862-869.
Kruger et al., Development of a microfluidic device for fluorescence activated cell sorting. J Micromech Microeng. Jun. 19, 2002;12:486-494.
Larsen et al., Microchip Coulter Particle Counter. Transducers '97, 1997 International Conference on Solid-State Sensors and Actuators. pp. 1319-1322, Jun. 16-19, 1997.
Lee et al., Hydrodynamic Focusing for a Micromachined Flow Cytometer. Transactions of the ASME. Sep. 2001;123:672-679.
Lee et al., Micro flow cytometers with buried SU-8/SOG optical waveguides. Sensors and Actuators A. Jan. 15, 2003;103(1-2):165-170.
McClain et al., Flow Cytometry of Escherichia coli on Microfluidic Devices. Anal Chem. Nov. 2001;73:5334-5338.
Miyake et al., Investigation of Sheath Flow Chambers for flow Cytometers (Micro Machined Flow Chamber with Low Pressure Loss). JSME International Journal. Series B. Feb. 1997;40(1):106-113.
Molho et al., Designing Corner Compensation for Electrophoresis in Compact Geometries. Micro Total Analysis Systems. A. van den Berg (Ed.), Kluwer Academic Pulbishers. pp. 287-290, (2000).
Molho et al., Fluid Transport Mechanisms in Microfluidic Devices. ASME International Mechanical Engineering Congress and Exposition. 8 pages, (1998).
Nieuwenhuis et al., Dynamic particle-shape measurements using a near-field optical sensor. Sensors. Jun. 12-14, 2002;130-133.
Nieuwenhuis et al., Integrated Flow-Cells for Adjustable Sheath Flows. The Society for Microelectronics—Annual Report 2003. pp. 225-231, Sep. 2004.
Shoji et al., Particles and molecules handling in micro channels. Lab-on-a-Chip. R.E. Oosterbroek (Ed.), Elsevier B.V. pp. 205-214, (2003).
St. John et al., Metrology and Simulation of Chemical Transport in Microchannels. Proceedings of the 8th IEEE Solid-State Sensor and Actuator Workshop. Jun. 7-11, 1998;98:106-111.
Watson, The Early Fluidic and Optical Physics of Cytometry. Cytometry (Communications in Clinical Cytometry). Feb. 1999;38:2-14.
Wolff et al., Chip-Integrated Microfluidic System for Cell Sorting and Cell Culturing. Eurosensors XIV, the 14th European Conference on Solid-State Transducers. pp. 235-238, Aug. 27-30, 2000.
Comparison of Specifications in U.S. Pat. No. 6,506,609 (Ex. 1006) and U.S. Appl. No. 09/569,747 (Ex. 1008). Oct. 5, 2017, 60 pages.
Cytonome/St, LLC's Preliminary Response. ABS Global, Inc., v. Cytonome/St, LLC, Case No. IPR2017-02097, dated Jan. 18, 2018, 72 pages.
Cytonome/St, LLC's Preliminary Response. ABS Global, Inc., v. Cytonome/St, LLC, Case No. IPR2017-02161, dated Jan. 11, 2018, 69 pages.
Cytonome/St, LLC's Preliminary Response. ABS Global, Inc., v. Cytonome/St, LLC, Case No. IPR2017-02162, dated Jan. 11, 2018, 52 pages.
Cytonome/St, LLC's Preliminary Response. ABS Global, Inc., v. Cytonome/St, LLC, Case No. IPR2017-02163, dated Jan. 18, 2018, 69 pages.
Decision Denying Institution of Inter Partes Review, 37 C.F.R. § 42.108. ABS Global, Inc. v. Cytonome/St, LLC. Case IPR2017-02161, U.S. Pat. No. 7,611,309. Entered Apr. 9, 2018. 32 pages.
Decision Denying Institution of Inter Partes Review, 37 C.F.R. § 42.108. ABS Global, Inc. v. Cytonome/St, LLC. Case IPR2017-02163, U.S. Pat. No. 7,311,476. Entered, Apr. 9, 2018. 28 pages.
Decision Granting Institution of Inter Partes Review, 37 C.F.R. § 42.108. ABS Global, Inc. v. Cytonome/St, LLC. Case IPR2017-02097, U.S. Pat. No. 8,529,161. Entered Apr. 17, 2018. 39 pages.
Decision Granting Institution of Inter Partes Review, 37 C.F.R. § 42.108. ABS Global, Inc. v. Cytonome/St, LLC. Case IPR2017-02162, U.S. Pat. No. 9,446,912. Entered Apr. 10, 2018. 26 pages.
Declaration of Dino Di Carlo, Ph.D. Case No. IPR2017-02097, ABS Global, Inc. vs. Cytonome/St, LLC. Oct. 5, 2017. 115 pages.
Declaration of Dino Di Carlo, Ph.D. Case No. IPR2017-02161, ABS Global, Inc. vs. Cytonome/St, LLC. Oct. 5, 2017. 105 pages.
Declaration of Dino Di Carlo, Ph.D. Case No. IPR2017-02162, ABS Global, Inc. vs. Cytonome/St, LLC. Oct. 5, 2017. 105 pages.
Declaration of Dino Di Carlo, Ph.D. Case No. IPR2017-02163, ABS Global, Inc. vs. Cytonome/St, LLC. Oct. 5, 2017. 101 pages.
Declaration of Ravi Kapur, Ph.D. Case No. IPR2017-02097, ABS Global, Inc. vs. Cytonome/St, LLC. Jan. 17, 2018. 17 pages.
Declaration of Ravi Kapur, Ph.D. Case No. IPR2017-02161, ABS Global, Inc. vs. Cytonome/St, LLC. Jan. 10, 2018. 17 pages.
Declaration of Ravi Kapur, Ph.D. Case No. IPR2017-02162, ABS Global, Inc. vs. Cytonome/St, LLC. Jul. 31, 2018. 30 pages.
Declaration of Ravi Kapur, Ph.D. Case No. IPR2017-02163, ABS Global, Inc. vs. Cytonome/St, LLC. Jan. 17, 2018. 15 pages.
Defendants' Answer and Counterclaims. Case: 3:17-cv-00446-wmc, Inguran, LLC d/b/a Stgenetics, XY, LLC, and Cytonome/St, LLC v. ABS Global, Inc., Genus PLC, and Premium Genetics (UK) Ltd., filed Oct. 18, 2017. 97 pages.
Defendants' Identification of Claim Terms and Proposed Constructions. Inguran, LLC d/b/a Stgenetics, XY, LLC, and Cytonome/St, LLC v. ABS Global, Inc. Genus PLC, and Premium Genetics (UK) Ltd. Case No. 17-cv-446. 7 pages, Apr. 12, 2018.
Defendants' Initial Invalidity Contentions Regarding U.S. Pat. Nos. 7,331,476, 7,661,309, 8,529,161, 9,446,912, 7,208,265, 9,365,822, and 9,524,860. Inguran, LLC d/b/a Stgenetics, XY, LLC, and Cytonome/St, LLC v ABS Global, Inc., Genus PLC, and Premium Genetics (UK) Ltd. Case No. 17-cv-446. 675 pages, dated Mar. 8, 2018.
Defendants' Response to Plaintiffs' Identification of Claim Terms and Proposed Constructions. Inguran, LLC d/b/a Stgenetics, XY, LLC, and Cytonome/St, LLC v ABS Global, Inc., Genus PLC, and Premium Genetics (UK) Ltd., Case No. 17-cv-446. 6 pages, dated May 10, 2018.
Exhibit A, Case: 3:17-cv-00446-wmc, filed Oct. 18, 2017, 8 pages.
Exhibit B, Case: 3:17-cv-00446-wmc, filed Oct. 18, 2017, 10 pages.
U.S. Appl. No. 10/979,848, filed Nov. 1, 2004, now U.S. Pat. No. 7,311,476, issued.
U.S. Appl. No. 11/998,557, filed Nov. 30, 2007, now U.S. Pat. No. 7,611,309, issued.
U.S. Appl. No. 12/610,753, filed Nov. 2, 2009, now U.S. Pat. No. 7,997,831, issued.
U.S. Appl. No. 13/179,084, filed Jul. 8, 2011, now U.S. Pat. No. 8,529,161, issued.
U.S. Appl. No. 13/968,962, filed Aug. 16, 2013, now U.S. Pat. No. 9,446,912, issued.
U.S. Appl. No. 15/269,556, filed Sep. 19, 2016, now U.S. Pat. No. 9,802,767, issued.
U.S. Appl. No. 15/797,790, filed Oct. 30, 2017, publication No. 2018-0208412, published.
Cytonome/ST, LLC, the assignee of the instant application, is a party to the case of *Inguran, LLC d/b/a STGenetics, XY, LLC, and Cytonome/ST, LLC v. ABS Global, Inc., Genus PLC, and Premium*

(56) References Cited

OTHER PUBLICATIONS

*Genetics (UK) Ltd* in the United States District Court for the Western District of Wisconsin, Civil Action No. 17-cv-446.
Cytonome/ST, LLC is the Assignee of U.S. Pat. No. 8,529,161. The '161 Patent is involved in ongoing Inter Partes Review proceedings under case number IPR2017-02097.
Cytonome/ST, LLC is the Assignee of U.S. Pat. No. 7,611,309. The '309 Patent was involved in an Inter Partes Review proceeding under case number IPR2017-02161 (Institution Denied).
Cytonome/ST, LLC is the Assignee of U.S. Pat. No. 9,446,912. The '912 Patent is involved in ongoing Inter Partes Review proceedings under case number IPR2017-02162.
Cytonome/ST, LLC is the Assignee of U.S. Pat. No. 7,311,476. The '476 Patent was involved in an Inter Partes Review proceeding under case number IPR2017-02163 (Institution Denied).
U.S. Appl. No. 13/830,316, filed Mar. 14, 2013, published, publication No. 2014-0273192.
Bunner, Deposition, (redacted). *Inguran, LLC vs. ABS Global, Inc., et al.,* Case No. 17-CV-446. 432 pages, Jun. 15, 2018.
Deshpande, Deposition, (redacted). *Inguran, LLC vs. ABS Global, Inc., et al.,* Case No. 17-CV-446. 408 pages, Jun. 14, 2018.
Gilbert, Deposition, (redacted). *Inguran, LLC vs. ABS Global, Inc., et al.,* Case No. 17-CV-446. 97 pages, Jun. 1, 2018.
Nieuwenhuis et al., Dynamic particle-shape measurements using a near-field optical sensor. Sensors. 2002 Jun. 12-14;130-133.
Opinion and Order, *Inguran, LLC, Cytonome/St, LLC, and XY, LLC v. ABS Global, Inc., Genus PLC, and Premium Genetics (UK) Ltd.* 17-cv-446-wmc. 61 pages, Apr. 29, 2019.
Final Written Decision, *ABS Global, Inc. v. Cytonome/St, LLC*, Case No. IPR2017-02162, U.S. Pat. No. 9,446,912. 38 pages, Apr. 8, 2019.
Final Written Decision, *ABS Global, Inc. v. Cytonome/St, LLC*, Case No. IPR2017-02097, U.S. Pat. No. 8,529,161. 52 pages, Apr. 16, 2019.
Decision, Denying Petitioner's Request for Rehearing, *ABS Global Inc. v. Cytonome/St, LLC*. Case No. IPR2017-02161, U.S. Pat. No. 7,611,309. 9 pages, Dec. 13, 2018.
Decision, Denying Petitioner's Request for Rehearing, *ABS Global Inc. v. Cytonome/St, LLC*. Case No. IPR2017-02163, U.S. Pat. No. 7,311,476. 5 pages, Dec. 14, 2018.
Exhibit A, Case: 3:17-cv-00446-wmc, filed Feb. 12, 2019, 82 pages.
Opinion and Order for Case: 3:17-cv-00446-wmc, *Inguran, LLC, Cytonome/St, LLC, and XY, LLC , v. ABS Global, Inc., Genus PLC, and Premium Genetics (UK) Ltd.* 26 pages, Feb. 26, 2019.
Bardell et al., Microfluidic Disposables for Cellular and Chemical Detection - CFD. Model Results and Fluidic Verification Experiments. BIOS 2001 The International Symposium on Biomedical Optics. SPIE. May 21, 2001;4265:1-13.

Chen et al., Microfluidic Switch for Embryo and Cell Sorting. The 12th International Conference on Solid State Sensors, Actuators and Microsystems. Jun. 8-12, 2003, pp. 659-662.
Chiu et al., Universally applicable three-dimensional hydrodynamic microfluidic flow focusing. Lab Chip. Feb. 22, 2013;13:1803-1809.
Dittrich et al., An Integrated Microfluidic System for Reaction, High-Sensitivity Detection, and Sorting of Fluorescent Cells and Particles. Anal Chem. Sep. 16, 2003;75(21):5767-5774.
Harding et al., Using the Microcyte flow cytometer to monitor cell number, viability, and apoptosis in mammalian cell culture. Biotechnol Prog. Sep.-Oct. 2000;16(5):800-2.
Huh et al., Use of Air-Liquid Two-Phase Flow in Hydrophobic Microfluidic Channels for Disposable Flow Cytometers. Biomedical Microdevices. May 2002;4(2):141-149.
Ichiki et al., On-Chip Cell Sorter for Single Cell Expression Analysis. Micro Total Analysis Systems. Oct. 21-25 2001, pp. 271-273.
Lee et al., Hydrodynamic Focusing for a Micromachined Flow Cytometer. J Fluids Eng. Apr. 18, 2001;123(3):672-679.
Lee et al., Micromachined pre-focused 1xN flow switches for continuous sample injection. Journal of Micromechanics and Microengineering. Aug. 9, 2001;11(5):567-573.
Lee et al., Micromachined pre-focusedM x N flow switches for continuous multi-sample injection. J Micromech Microeng. Oct. 12, 2001;11:654-661.
Lin et al., Vertical focusing device utilizing dielectrophoretic force and its application on microflow cytometer. Journal of Microelectromechanical Systems. Dec. 2004;13(5):923-932.
Shirasaki et al., On-chip cell sorting system using laser-induced heating of a thermoreversible gelation polymer to control flow. Anal Chem. Feb. 1, 2006;78(3):695-701.
Simonnet et al., High-throughput and high-resolution flow cytometry in molded microfluidic devices. Anal Chem. Aug. 15, 2006;78(16):5653-63.
Sundararajan et al., Three-dimensional hydrodynamic focusing in polydimethylsiloxane (PDMS) microchannels. Journal of Microelectromechanical Systems. Aug. 2004;13(4):559-567.
Telleman et al., Cell Sorting in Microfluidic Systems. Micro Total Analysis Sytems '98. Oct. 13-16, 1998. Pages 39-44.
Tung et al., PDMS-based opto-fluidic micro flow cytometer with two-color, multi-angle fluorescence detection capability using PIN photodiodes. Sensors and Actuators B: Chemical. Mar. 2004;98(2-3):356-367.
Tung et al., Small volume low mechanical stress cytometry using computer-controlled Braille display microfluidics. Lab Chip. Nov. 2007;7(11):1497-503.
Wang et al., Measurements of scattered light on a microchip flow cytometer with integrated polymer based optical elements. Lab Chip. Aug. 2004;4(4):372-7.
Wolff et al., Rare Event Cell Sorging in a Microfluidic System for Application in Prenatal Diagnosis. Micro Total Analysis Systems '98, Oct. 13-16, 1998. pp. 77-80.
New Zealand Office Action for Application No. 743491, dated Mar. 8, 2019, 3 pages.

* cited by examiner

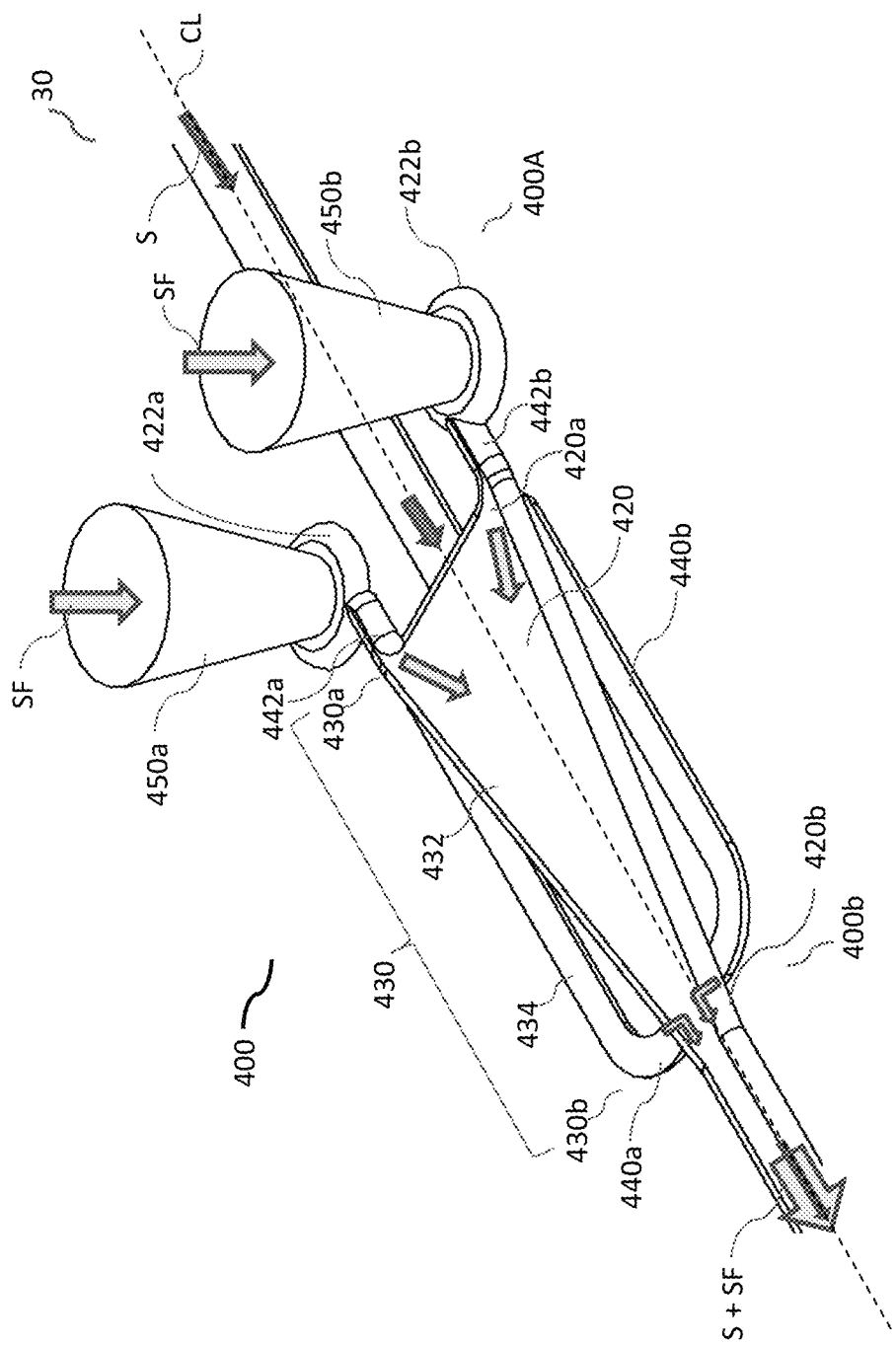

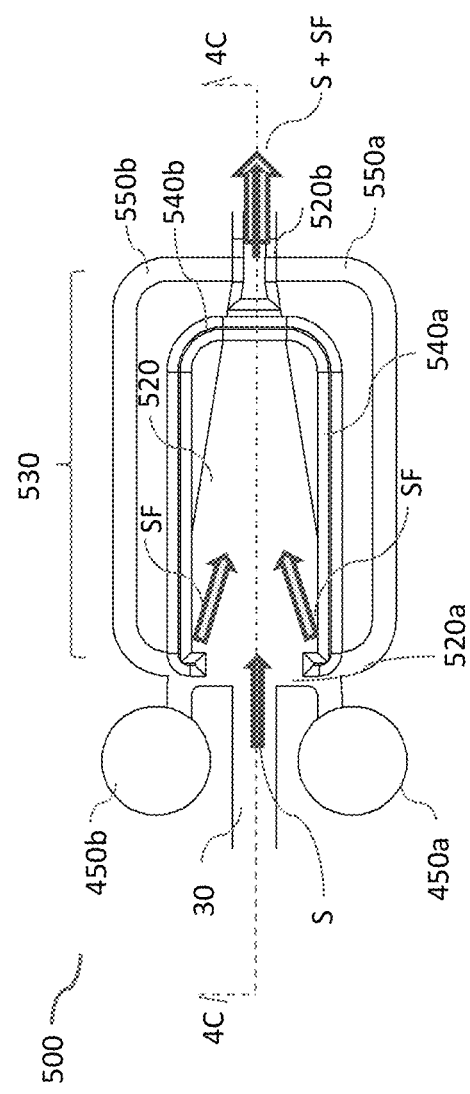

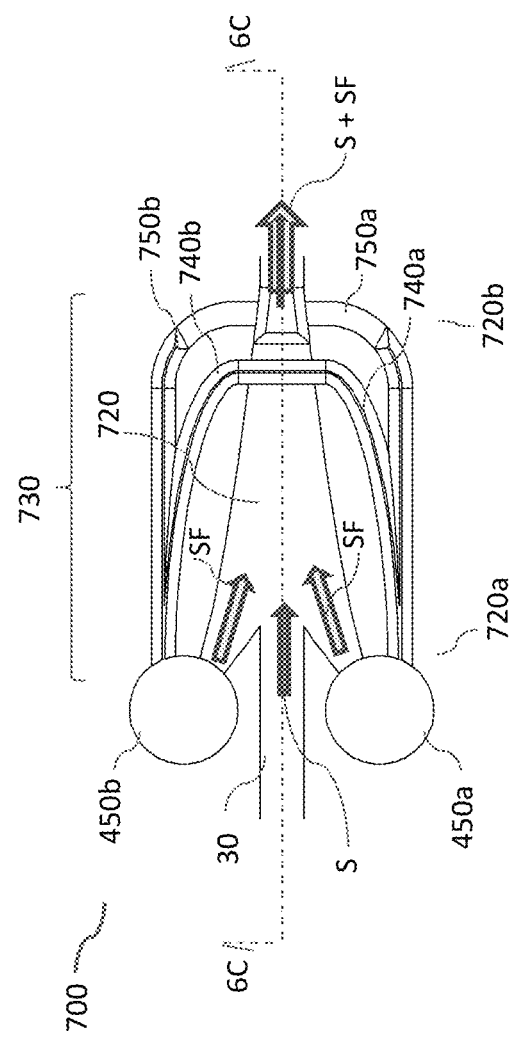

HYDRODYNAMIC FOCUSING APPARATUS AND METHODS

RELATED APPLICATIONS

This application claims the benefit of priority to U.S. Provisional Application Ser. No. 61/785,734, titled "Hydrodynamic Focusing Apparatus and Methods," and filed Mar. 14, 2013, the content of which is hereby incorporated by reference in its entirety.

TECHNICAL FIELD

Generally, this disclosure relates to hydrodynamic focusing, in particular, in a microfluidic device. More specifically, the present disclosure relates to systems and methods for producing a sheath flow in a flow channel and, in particular, in a micro channel in a microfluidic device.

BACKGROUND

Sheath flow is a particular type of laminar flow in which one layer of sample fluid, or a particle, is surrounded by another layer of focusing fluid on more than one side. The process of confining a particle stream in a fluid is referred to as a 'sheath flow' configuration. For example, in a sheath flow configuration, a sheath fluid may envelop and pinch a sample fluid containing a number of particles. The flow of the sample fluid containing particles suspended therein may be narrowed almost to the outer diameter of particles in the center of the sheath fluid. The resulting sheath flow flows in a laminar state within an orifice or channel so that the particles are aligned and accurately pass through an orifice or channel in a single file row.

Sheath flow is used in many applications where it is preferable to protect particles or fluids by a layer of sheath fluid, for example in applications wherein it is necessary to protect particles from air. For example, in particle sorting systems, flow cytometers and other systems for analyzing a sample, particles to be sorted or analyzed are usually supplied to a measurement position in a central fluid current, which is surrounded by a particle free liquid sheath.

Sheath flow is useful because it can position particles with respect to sensors or other components and prevent particles in the center fluid, which is surrounded by the sheath fluid, from touching the sides of the flow channel and thereby prevents clogging of the channel. Sheath flow allows for faster flow velocities and higher throughput of sample material. Faster flow velocity is possible without shredding cells in the center fluid because the sheath fluid protects the cells from potentially high shear forces at the walls of the flow channel.

Conventional devices that have been employed to implement sheath flow have relatively complex designs and are relatively difficult to fabricate.

SUMMARY

According to aspects of the disclosure, a microfluidic particle processing assembly including a substrate and a flow channel formed in the substrate may be provided. The flow channel may include an inlet, a fluid focusing region having an associated fluid focusing feature for focusing a particle within the flow channel, and an inspection region at least partially downstream of the fluid focusing region. Further, the flow channel may have first and second outlets.

According to other aspects, the fluid focusing features of the flow channel focusing region may include a core stream forming geometry. The core stream forming geometry may further include a lateral fluid focusing region, a first vertical fluid focusing component, and a second vertical fluid focusing component.

According to some aspects, the first vertical fluid focusing component may include a vertical fluid focusing channel and the second vertical fluid focusing component may include a second vertical fluid focusing channel. The first vertical fluid focusing component and the second vertical fluid focusing component may be in communication with the fluid focusing region in opposite vertical directions. The first vertical fluid focusing component may provide a first vertical influence and the second vertical fluid focusing component may provide a second vertical influence in the opposite directions as the first vertical influence.

According to other aspects, the flow channel may further include a sheath inlet in fluid communication with the sheath source. A sample inlet may be positioned within a sheath flow created by the sheath inlet to facilitate a co-axial flow of sheath and sample. The sample inlet may include a tapered or beveled inlet.

According to yet other aspects, the flow channel may have a first width and a first height at the sample inlet. The flow channel may a second width and a second height at a first transition point. The height of the flow channel may be reduced between the sample inlet and the first transition point. The flow channel may have a third width and a third height at a second transition point. The height of the flow channel may remain constant between the first transition point and the second transition point and the width of the flow channel may be reduced between the first transition point and the second transition point. The third height and the third width of the flow channel may be maintained through the inspection region. The flow channel may transition from a square cross section to a rectangular cross section. The flow channel may transition from a circular cross section to an elliptical cross section.

The microfluidic assembly may further include a plurality of flow channels as presented herein.

According to other aspects, the fluid focusing feature of the fluid focusing region may further include ultrasonic transducers for producing pressure waves in the focusing region of each flow channel. The ultrasonic transducers may be an array of ultrasonic transducers for producing a standing pressure wave along the flow channel.

According to even other aspects, a diverting mechanism in communication with the flow channel may be provided. The diverting mechanism may include a bubble valve. Alternatively, the diverting mechanism may include an array of ultrasonic and/or standing acoustic wave transducers. Optionally, the diverting mechanism may include interdigitated transducers (IDT).

According to certain aspects, a microfluidic chip may include a substantially planar chip substrate having an upper surface and a lower surface. A microfluidic flow channel may be provided within the chip substrate. A first inlet port may be formed on the upper surface of the chip substrate for receiving a focusing fluid. The first inlet port may be in fluid communication with the microfluidic flow channel. The microfluidic flow channel may include a first focusing fluid inlet configured to introduce focusing fluid from the first inlet port into the microfluidic channel in a first direction, a second focusing fluid inlet configured to introduce focusing fluid from the first inlet port into the microfluidic channel in a second direction, and a third focusing fluid inlet configured to introduce focusing fluid from the first inlet port into the microfluidic channel in a third direction.

According to certain other aspects, the microfluidic chip may also include a second inlet port formed on the upper surface of the chip substrate for receiving a focusing fluid. The second inlet port may be in fluid communication with the microfluidic flow channel. The microfluidic flow channel may include a fourth focusing fluid inlet configured to introduce focusing fluid from the second inlet port into the microfluidic channel in a fourth direction. The second focusing fluid inlet may be configured to introduce focusing fluid from the second inlet port into the microfluidic channel in the second direction, and the third focusing fluid inlet may be configured to introduce focusing fluid from the second inlet port into the microfluidic channel in the third direction.

The microfluidic flow channel may include a fluid flow focusing region having an upstream end region and a downstream end region. The first focusing fluid inlet may be configured to introduce focusing fluid into the fluid flow focusing region in the upstream end region. The second and third focusing fluid inlets may be configured to introduce focusing fluid into the fluid flow focusing region in the downstream end region.

According to other aspects, a microfluidic chip may include a substantially planar substrate having an upper surface and a lower surface. A microfluidic channel may be formed in the substantially planar substrate and may have an upper surface and a lower surface. An inlet port may be formed on the upper surface of the substantially planar substrate and may be configured to receive a focusing fluid. A first focusing fluid channel in fluid communication with the inlet port may be provided. The first focusing fluid channel may be configured to introduce focusing fluid into the microfluidic channel via a first aperture in the upper surface of the microfluidic channel. A second focusing fluid channel in fluid communication with the inlet port may be provided. The second focusing fluid channel may be configured to introduce focusing fluid into the microfluidic channel via a second aperture in the lower surface of the microfluidic channel.

The microfluidic channel and the first and second focusing fluid channels may be formed when a lower surface of an upper substrate layer and an upper surface of a lower substrate layer are joined together.

The microfluidic channel may lie in a first plane upstream of the first aperture and in a second plane downstream of the second aperture.

At least one outlet port may be formed on the upper surface of the substantially planar substrate and in fluid communication with the fluid flow focusing region.

Certain embodiments of the disclosed apparatus and methods are summarized below. These embodiments are not intended to limit the scope of the disclosure, but rather serve as brief descriptions of exemplary embodiments. Both the disclosure and claimed invention may encompass a variety of forms which differ from these summaries.

BRIEF DESCRIPTION OF THE DRAWINGS

Exemplary embodiments of the present disclosure are further described with reference to the appended figures. It is to be noted that the various features and combinations of features described below and illustrated in the figures can be arranged and/organized differently to result in embodiments which are still within the spirit and scope of the present disclosure. To assist those of ordinary skill in the art in making and using the disclosed systems, assemblies and methods, reference is made to the appended figures.

FIG. 3A is a top perspective view of a portion of a flow channel geometry with arrows schematically depicting flow of sample fluid and focusing fluid in accordance with certain embodiments described herein.

FIG. 4B is top view of a portion of a flow channel geometry in accordance with the embodiment of FIG. 4A.

FIG. 6B is top view of a portion of a flow channel geometry in accordance with the embodiment of FIG. 6A.

Figure 1:
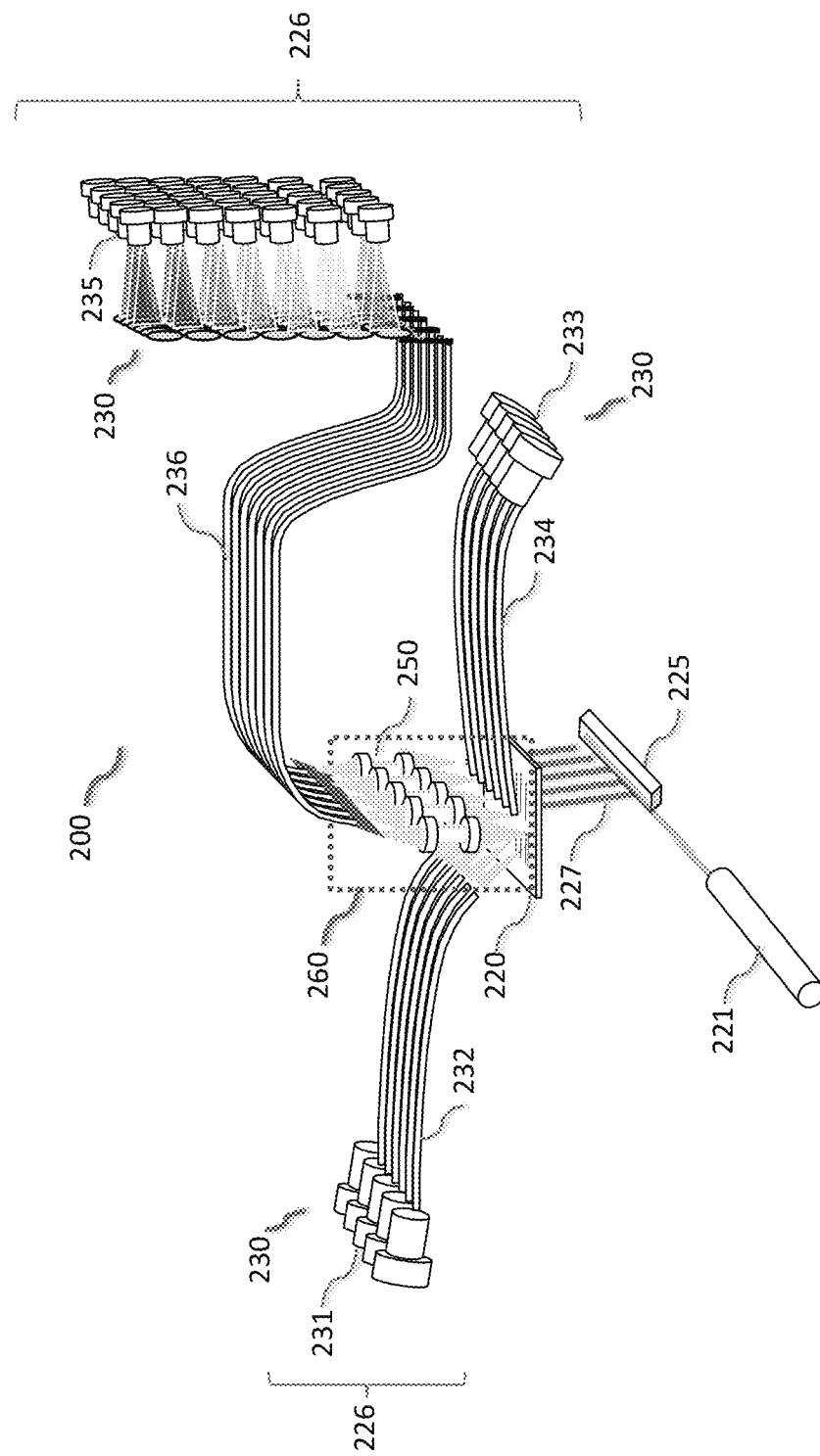
FIG. 1 schematically illustrates an exemplary particle processing system according to the present disclosure.

While the present disclosure may be embodied with various modifications and alternative forms, specific embodiments are illustrated in the figures and described herein by way of illustrative examples. It should be understood the figures and detailed descriptions are not intended to limit the scope of the claims to the particular form disclosed, but that all modifications, alternatives, and equivalents falling within the spirit and scope of the claims are intended to be covered.

DETAILED DESCRIPTION

A microfluidic particle (e.g., cell) analysis and/or sorting system for a microfluidic chip, in accordance some embodiments, may have a wide variety of applications as a therapeutic medical device enabling cell-based therapies, such as blood transfusion, bone marrow transplants, and/or mobilized peripheral blood implants. Embodiments of microfluidic sorting systems may be capable of selecting cells based on intrinsic characteristics as determined by interaction of light with the cells (e.g., scatter, reflection, and/or auto fluorescence) independent of protocols and necessary reagents. A microfluidic system may employ a closed, sterile, disposable cartridge including a microfluidic chip. The microfluidic system may process particles (e.g., cells) at high speeds, and deliver particles (e.g., cells) with high yield and high purity.

Certain embodiments described herein relate systems and methods for producing a sheath flow in a flow channel and, in particular, in a micro channel in microfluidic devices.

As used herein, the term "particles" includes, but is not limited to, cells (e.g., blood platelets, white blood cells, tumorous cells, embryonic cells, spermatozoa, etc.), synthetic beads (e.g., polystyrene), organelles, and multi-cellular organisms. Particles may include liposomes, proteoliposomes, yeast, bacteria, viruses, pollens, algae, or the like. Particles may also refer to non-biological particles. For example, particles may include metals, minerals, polymeric substances, glasses, ceramics, composites, or the like. Additionally, particles may include cells, genetic material, RNA, DNA, fragments, proteins, etc. or bead, for example, with fluorochrome conjugated antibodies.

As used herein, the term "microfluidic system" refers to a system or device including at least one fluidic channel having microscale dimensions. The microfluidic system may be configured to handle, process, detect, analyze, eject, and/or sort a fluid sample and/or particles within a fluid sample. The term "channel" as used herein refers to a pathway formed in or through a medium that allows for movement of fluids, such as liquids and gases. The term "micro channel" refers to a channel, preferably formed in a microfluidic system or device, having cross-sectional dimensions in the range between about 1.0 μm and about 2000 μm, preferably between about 25 μm and about 500 μm, and most preferably between about 50 μm and about 300 μm. One of ordinary skill in the art will be able to determine an appropriate volume and length of the micro channel for the desired application. The ranges above are intended to include the above-recited values as upper or lower limits. The micro channel may have any selected cross-sectional shape or arrangement, non-limiting examples of which include a linear or non-linear configuration, a U-shaped or D-shaped configuration, and/or a rectangular, triangular, elliptical/oval, circular, square, or trapezoidal geometry. A microfluidic device or microfluidic chip may include any suitable number of micro channels for transporting fluids. A microfluidic chip may be provided as a disposable cartridge with a closed channel system.

As used herein the terms "vertical," "lateral," "top," "bottom," "above", "below," "up," "down," and other similar phrases should be understood as descriptive terms providing general relationship between depicted features in the figures and not limiting on the claims, especially relating to flow channels and microfluidic chips described herein, which may be operated in any orientation.

The present disclosure bears relations to U.S. Pat. No. 7,311,476 which is hereby incorporated by reference.

Referring now to FIG. 1, a particle processing system 200 may be configured, dimensioned and adapted for analyzing, sorting, and/or processing (e.g., purifying, measuring, isolating, detecting, monitoring and/or enriching) particles (e.g., cells, microscopic particles, etc.) or the like. For example, system 200 may be a cytometer and/or a cell purification system or the like, although the present disclosure is not limited thereto. Rather, system 200 may take a variety of forms, and it is noted that the systems and methods described may be applied to other particle processing systems.

In exemplary embodiments, system 200 is a microfluidic flow sorter particle processing system (e.g., microfluidic chip based system) or the like. Exemplary microfluidic flow sorter particle processing systems and components or the like are disclosed, for example, in U.S. Pat. No. 8,529,161 (Ser. No. 13/179,084); U.S. Pat. No. 8,277,764 (Ser. No. 11/295,183); U.S. Pat. No. 8,123,044 (Ser. No. 11/800,469); U.S. Pat. No. 7,569,788 (Ser. No. 11/101,038); U.S. Pat. No. 7,492,522 (Ser. No. 11/906,621) and U.S. Pat. No. 6,808,075 (Ser. No. 10/179,488); and US Patent Publication Nos. 2012/0277902 (Ser. No. 13/342,756); 2011/0196637 (Ser. No. 13/022,525) and 2009/0116005 (Ser. No. 12/259,235); and U.S. Patent Application Ser. Nos. 61/647,821 (Ser. No. 13/896,213) and 61/702,114 (Ser. No. 14/029,485), 61/784,323, the foregoing being incorporated herein by reference in their entireties.

In further exemplary embodiments, system 200 may be a multi-channel or multi-jet flow sorter particle processing system (e.g., multiple capillaries or multiple fluid jet-based systems) or the like. Exemplary multi-channel or multi-jet flow sorter particle processing systems and components or the like are disclosed, for example, in US Patent Publication No. 2005/0112541 (Ser. No. 10/812,351), the entire contents of which is hereby incorporated by reference in its entirety.

FIG. 1 illustrates a system 200 suitable for implementing an illustrative embodiment of the present disclosure. System 200 includes a microfluidic assembly 220. Microfluidic assembly 220 includes and/or is in communication with a particle inspection region and a sample fluid input region. Microfluidic assembly 220 may include a plurality of micro channels for conveying a substance, such as particles or cells, therethrough. In certain embodiments and as can be understood by those familiar in the art, microfluidic assembly 220 may be a combination of microfluidic chips, micro channels, cuvettes, capillaries, nozzles, or jets which may combine to produce a multichannel particle processing system. The micro channels transport fluid and/or particles through the assembly 220 for processing, handling, and/or performing any suitable operation (e.g., on a liquid sample). Assembly 220 may include any suitable number of micro channels for transporting fluids through assembly 220.

In exemplary embodiments, an optical detector system 226 for use with microfluidic assembly 220 may be provided. Optical detector system 226 may be configured for the interrogation of the particles flowing through or located within an interrogation region. Further, optical detector system 226 may monitor flow through a plurality of channels simultaneously. In exemplary embodiments, system 226 can inspect individual particles for one or more particular characteristics, such as size, form, fluorescence, optical scattering, as well as other characteristics.

System 200 also includes at least one electromagnetic radiation or light source 221 (e.g., a laser source or the like) for simultaneously or sequentially illuminating at least a portion of each of an interrogation region. The electromagnetic radiation source 221 may be coupled to and/or in communication with beam shaping optics 225 (e.g., segmented mirror/mirrors or the like) for producing and forming a beam of electromagnetic radiation (e.g., light) 227. The light source 221 may be provide as one or more monochromatic light sources, polychromatic light sources, or any combination of the aforementioned. In general, the electromagnetic radiation source(s) 221 may have any suitable wavelength and one skilled in the art will recognize that any suitable light source(s) may be used.

In some embodiments, the one or more radiation beams 227 may pass through an optical mask aligned with a plurality of particle-conveying micro channels in the microfluidic assembly 220. The optical mask may take the form of an array of pinholes (e.g., provided in an optically opaque layer) associated with the interrogation regions of the plurality of micro channels. Other spatial and/or spectral filter arrays may be provided in the illumination and/or detection path of the particle processing system 200.

Examples of optical signals that may be produced in optical particle analysis, cytometry and/or sorting when a beam 227 intersects a particle include, without limitation, optical extinction, angle dependent optical scatter (forward and/or side scatter) and fluorescence. Optical extinction refers to the amount of electromagnetic radiation or light that a particle extinguishes, absorbs, or blocks. Angle dependent optical scatter refers to the fraction of electromagnetic radiation that is scattered or bent at each angle away from or toward the incident electromagnetic radiation beam. Fluorescent electromagnetic radiation may be electromagnetic radiation that is absorbed and/or scattered by molecules associated with a particle or cell and re-emitted at a different wavelength. In some instances, fluorescent detection may be performed using intrinsically fluorescent molecules.

In exemplary embodiments, optical detector system 226 may include one or more detector subsystems 230 to capture and observe the optical signals generated by the intersection of electromagnetic radiation beam 227 with a particle in a channel. Detector subsystems 230 may include one or more extinction detector assemblies 231 for capturing extinction signals, one or more scatter detector assemblies 233 for capturing scatter signals, and one or more fluorescence detector assemblies 235 for capturing fluorescence signals. In a preferred embodiment, detector system 226 may include at least one extinction detector assembly 231, at least one scatter detector assembly 233, and at least one fluorescence detector assembly 235. Detector assemblies 231, 233, 235 may include photomultipliers, photodiodes, cameras, or other suitable device(s).

According to certain aspects, a detector subsystem 230 may include one or more micro-lens systems 250. A plurality of micro-lens systems 250 may be provided as a micro-lens array 260. Further, detector subsystems 230 may include fiber optics or other waveguide-type optical transmission elements to direct the signals to the sensor elements, one or more lenses, filters, mirrors, and/or other optical elements to collect, shape, transmit, etc. the signal exiting the interrogation region 222 and being received by the detector subsystems 230.

According to certain embodiments, a single detector subsystem 230 may be associated with a plurality of interrogation sites (e.g., microfluidic channels) and thus, may receive signals (simultaneously, sequentially, overlapping, non-overlapping, etc.) from each of the plurality of interrogation sites. The detector subsystems 230 may be connected to electronics (not shown) to analyze the signals received from the detector assemblies and/or control one or more aspects of the particle sorting system 200.

Figure 2:
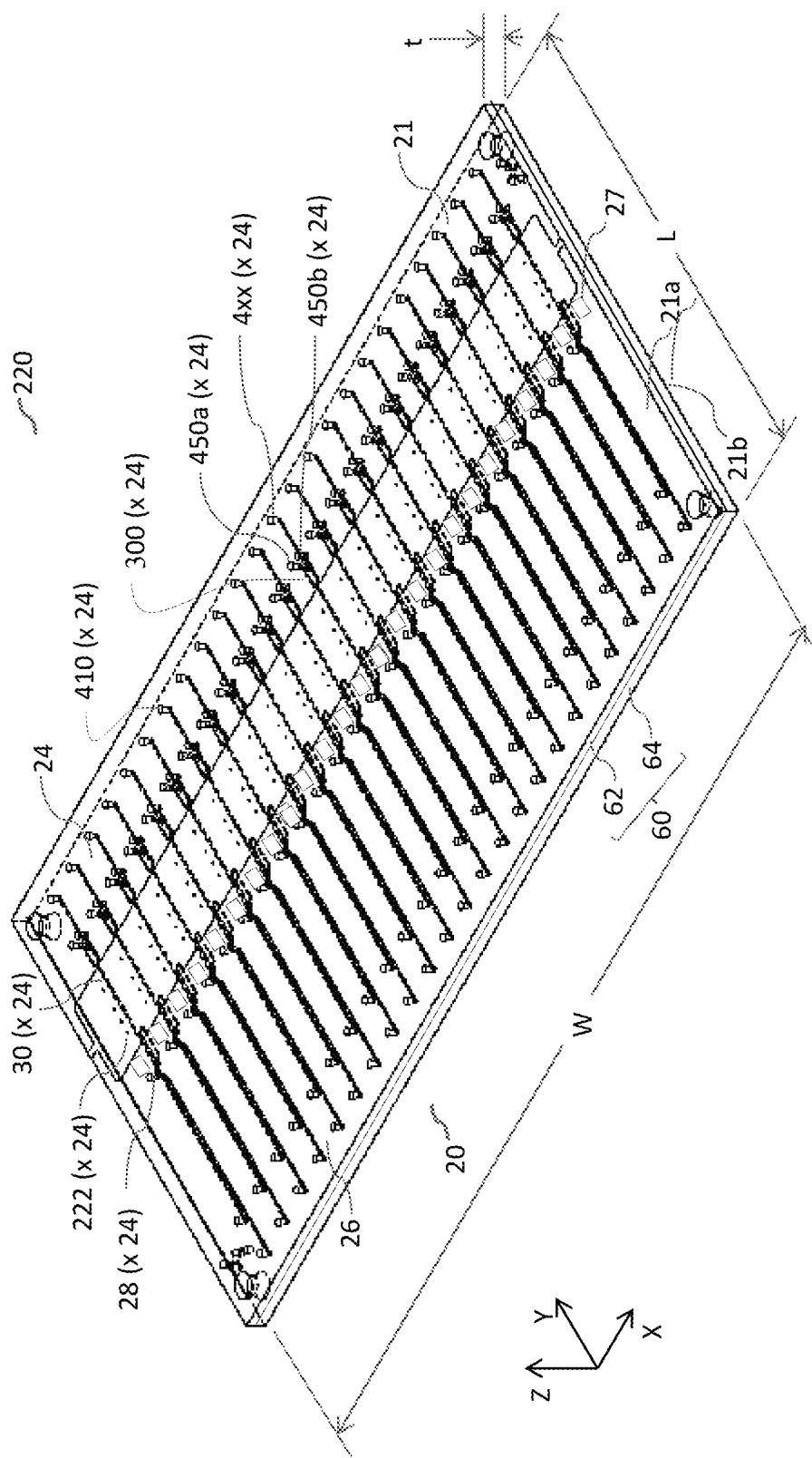
FIG. 2 illustrates an exemplary microfluidic chip according to the present disclosure.

According to certain embodiments and referring to FIG. 2, microfluidic assembly 220 may be configured as a microfluidic chip 20 and may include a substrate 21 having a plurality of channels 30 (e.g., micro channels) disposed or formed therein. The micro channels 30 may be configured to transport fluid and/or particles through the microfluidic chip 20 for processing, handling, and/or performing any suitable operation on a liquid sample (e.g., a particle sorting system). For example, each micro channel 30 may be a flow cytometer. According to certain aspects, the micro channels 30 may be arranged parallel to each other.

As best shown in FIG. 2, the microfluidic chip 20 may include an input region 24 in which a sample containing particles (e.g., cells, etc.) is input into the microfluidic chip 20 for processing and an output region 26 for removing the processed sample from the microfluidic chip 20. The substrate 21 may be provided as a substantially planar substrate, i.e., having a first dimension (e.g., thickness t) much less than its other two dimensions (e.g., length L and width W). Further, the substrate 21 of the microfluidic chip 20 may include first and second major plane surfaces: an upper surface 21a; and a lower surface 21b.

The sample fluid may be input via a sample inlet port 410 through the upper surface 21a of the microfluidic chip 20. Each micro channel 30 may have an interrogation region 222 associated therewith. Particles in channels 30 may be detected while flowing through the interrogation regions 222. At the interrogation region 222, individual particles may be inspected or measured for a particular characteristic, such as size, form, orientation, fluorescence intensity, etc. Interrogation regions 222 may be illuminated through the upper surface 21a and/or the lower surface 21b of the microfluidic chip 20.

The plurality of channels 30 may be evenly distributed (i.e., evenly spaced) across the width W of the microfluidic chip 20. According to certain embodiments, a centerline-to-centerline spacing between the channels 30 may range from 0.2 mm to 5.0 mm. The centerline-to-centerline spacing between the micro channels 30 may be less than 4.0 mm, less than 3.0 mm, or even less than 1.0 mm. According to certain embodiments, the centerline-to-centerline spacing between the micro channels 30 may range from 2.5 mm to 3.0 mm. Advantageously, to minimize the footprint of the microfluidic chip 20, the centerline-to-centerline spacing between the micro channels 30 may be less than 2.0 mm, less than 1.5 mm, or even less than 1.0 mm. According to certain embodiments, the centerline-to-centerline spacing between the micro channels 30 may range from 0.7 mm to 1.2 mm.

The substrate 21 of the microfluidic chip 20 may be formed with one or more substrate layers 60. As shown in FIG. 2, the substrate 21 may be formed by bonding or otherwise attaching an upper substrate layer 62 to a lower substrate layer 64. In general, any number of layers may be used to form microfluidic chip 20.

The substrate layers 60 of the microfluidic chip 20 may be glass (e.g., UV fused-silica, quartz, borofloat, etc.), PDMS, PMMA, COC, or any other suitably transmissive material. The thickness of the first substrate layer 62 may range from approximately 100 μm up to approximately 1000 μm. In certain preferred embodiments, the thickness of substrate layer 62 may range from approximately 200 μm up to approximately 600 μm. For example, the thickness of substrate layer 62 may be approximately 400 μm. In other preferred embodiments, the thickness of substrate layer 62 may range from approximately 500 μm up to approximately 900 μm. By way of non-limiting examples, the thickness of substrate layer 62 may be approximately 700 μm or approximately 750 μm. In certain embodiments, the microfluidic chip 20 may be formed with only two substrate layers 62, 64.

In the embodiment illustrated in FIG. 2, the microfluidic chip 20 includes twenty-four micro channels 30, although, in general, any number of micro channels 30 may be provided (e.g., as non-limiting examples, 2, 4, 8, 24, 36, 72, 144, or 288 channels). According to some embodiments, when microfluidic chip 20 has twenty-four micro channels 30, the microfluidic chip 20 may have an overall width W ranging from 70 mm to 80 mm.

According to certain embodiments, each of the plurality of micro channels 30 may include a sorting or diverting mechanism 28 for directing particles flowing within the channels 30 into various downstream channels. Sorting and/or diverting may be accomplished through one or more mechanisms, which may include but are not limited to: mechanical displacement of the particle by deflecting a membrane with a piezoelectric actuator, thermal actuators, optical force techniques, dielectric methods (e.g., dielectrophoretic), ultrasonic transducers 27 (both bulk and/or surface), surface acoustic wave actuators, and other suitable sort mechanisms or techniques. A surface acoustic wave actuator may be provided as an interdigitated transducer (IDT). Exemplary ultrasonic transducers are disclosed, for example, in U.S. patent Ser. Nos. 12/631,059 and 13/818,146, the entire contents of which are hereby incorporated by reference in their entirety.

The particle processing system 200 may include a receptacle or holder (not shown) for removably receiving microfluidic chip 20. Further, the particle processing system 200 may include one or more stages for positioning the microfluidic chip 20 relative to the optical detection system 226. The stages may allow for movement (translation and/or rotation) of the microfluidic chip 20.

According to aspects of the disclosure, a microfluidic chip having a micro channel for processing a sample fluid is provided. The micro channel 30 may be in fluid communication with one or more sample inlet ports 410 (see FIG. 2) configured to receive a sample fluid S. The sample inlet ports 410 may be in fluid communication with a sample reservoir, manifold, channel, well, test tube, etc. Further, the micro channel 30 may be in fluid communication with one or more focusing fluid inlet ports 450 (e.g., 450a and 450b) configured to receive a focusing fluid SF. The focusing fluid inlet ports 450 may be in fluid communication with a sheath fluid reservoir, manifold, channel, bag, bottle, container, etc.

According to aspects of the disclosure, the micro channel 30 may focus the sample by using focusing fluid (e.g., sheath fluid) and a core stream forming geometry 300, for example, defined in the substrate 21 of the microfluidic chip 20. The core stream forming geometry 300 may be used to laminarly focus, streamline, decelerate, and/or accelerate the flow of the sample fluid S with a surrounding sheath of focusing fluid SF. In some embodiments, the core stream forming geometry 300 may include a lateral fluid focusing component (see, for example, lateral fluid focusing component 432 of the embodiment of FIGS. 3A-E) and one or more vertical fluid focusing components (see, for example, vertical fluid focusing component 434 of FIGS. 3A-E). In the context of the embodiment of FIG. 2, "lateral" may refer to a direction extending generally in the plane of the substantially planar microfluidic chip 20 and "vertical" may refer to a direction extending generally out of the plane of the microfluidic chip 20.

Figure 3B:
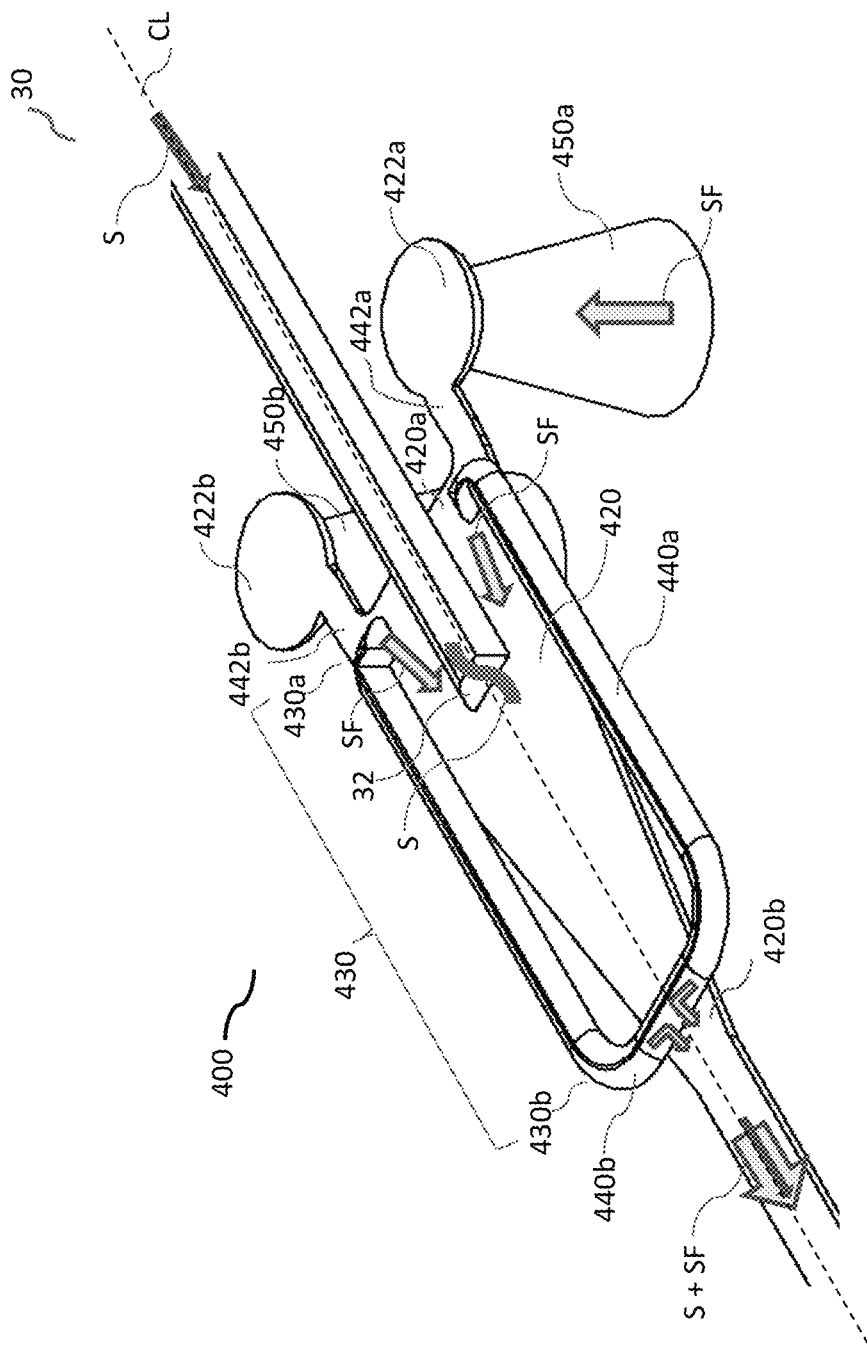
FIG. 3B is a bottom perspective view of a portion of a flow channel geometry in accordance with the embodiment of FIG. 3A, with arrows schematically depicting flow of sample fluid and focusing fluid in accordance with certain embodiments described herein.

Referring now to FIGS. 3A and 3B, a portion of a micro channel 30 having a core stream forming geometry 400 is shown. A sample fluid S flowing through the micro channel 30 may enter the core stream forming geometry 400 along a longitudinal centerline CL (when viewed from above) of the core stream forming geometry 400. Focusing fluid SF may enter the core stream forming geometry 400 symmetrically with respect to the longitudinal centerline CL of the core stream forming geometry 400. The focusing fluid may enter the core stream forming geometry 400 at an upstream region 400a of the core stream forming geometry and also at a downstream region of the core stream forming geometry 400b. The sample fluid S and the focusing fluid SF may be induced to flow through the micro channel 30 via any means known in the art, including one or more pumps (e.g., peristaltic pumps), ultrasonic drivers, etc.

The core stream forming geometry 400 may include a fluid focusing region 430 incorporated into a region of a flow channel 30 for generating a focused core stream flow wherein the focusing fluid SF shapes the sample stream S. The core stream forming geometry 400 is illustrated as interior surfaces of a flow channel 30 in a microfluidic chip 20, such as those microfluidic chips previously described. The illustrated core stream forming geometry 400 provides improved sheath flow capabilities and thus improved sample focusing capabilities. The core stream forming geometry 400 may be fabricated in plastics, polycarbonate, glass, metals, or other suitable materials using microfabrication, injection molding, stamping, machining, 3D printing or by other suitable fabrication techniques. As such, the core stream forming geometry 400 may be formed in a single substrate layer, or by a plurality of stacked layers.

Referring to FIGS. 3A and 3B, sheath inlets ports 450 may be provided with conical inlet shapes that are each received at a sheath aggregating volume 422. The sheath aggregating volumes 422 may be provided with a single outlet or sheath fluid channel 442, or multiple outlets or sheath fluid channels to further transport focusing fluid SF to flow channel 30 components. In some embodiments, there may not be any feature specifically identifiable as a sheath aggregating volume and focusing fluid may flow directly from sheath inlet ports 450 to a focusing fluid distribution network.

In FIGS. 3A and 3B, two sheath inlet ports 450a, 450b are associated with a single micro channel 30. Each sheath inlet port 450 may provided with a single port outlet or sheath fluid channel 440. Sheath fluid channel 440a is illustrated as extending from sheath fluid inlet port 450a and sheath fluid channel 440b is illustrated as extending from sheath fluid inlet port 450b. Each sheath fluid channel 440 extends from an upstream region 430a of the fluid focusing region 430 to a downstream region 430b of the fluid focusing region 430. Each sheath fluid channel 440 is configured to transport focusing fluid SF from a sheath inlet port 450 to the micro channel 20 in the downstream region 430b of the fluid focusing region 430. In the embodiment of FIGS. 3A-3E, the core stream forming geometry 400 is symmetrically formed relative to a longitudinal centerline CL of the micro channel 30 (when viewed from above).

According to alternative embodiments, a single sheath fluid inlet port 450 may be provided and a branched sheath fluid channel may be configured transport focusing fluid form the single sheath fluid inlet port 450 to a plurality of regions of the core stream forming geometry 400. Additionally, flow restrictions may be placed on one or more fluidic paths emanating from the sheath aggregating volume 422.

The fluid focusing region 430 may include a lateral fluid focusing component 432 and a vertical fluid focusing component 434, both of which may contribute to shaping the sample stream S and increasing the axial acceleration of both the focusing or sheath fluid FS and sample S through the flow channel 30. The lateral fluid focusing component may include a lateral fluid focusing chamber 420. The lateral fluid focusing chamber 420 is provided with sample fluid S from a portion of the micro channel 30 in fluid communication with the sample inlet port 410. Further, the lateral fluid focusing chamber 420 is provided with sheath or focusing fluid SF from the one or more sheath fluid inlet ports 450.

According to the embodiment of FIGS. 3A-3E, the lateral fluid focusing chamber 420 is widest at its upstream end 420a and narrowest at its downstream end 420b. Between the upstream end 420a and the downstream end 420b, the chamber 420 substantially linearly tapers symmetrically with respect to the centerline CL in the lateral direction. Between the upstream end 420a and the downstream end 420b, the chamber 420 has a substantially constant thickness. Further, the upstream end 420a is provided as a substantially flat wall having two openings, one at each corner, for admitting focusing fluid SF.

Thus, as illustrated, two sheath inlet ports 450a, 450b may symmetrically introduce focusing fluid SF into the lateral fluid focusing chamber 420. In FIGS. 3A-3E, a relatively short channel 442a extends between the sheath aggregating volume 422a and the corner opening of the lateral fluid focusing chamber 420. Similarly, a relatively short channel 442b extends between the sheath aggregating volume 422b and laterally opposed corner opening of the lateral fluid focusing chamber 420. Thus, focusing fluid SF enters chamber 420 from opposed lateral edges (or lateral sides) of the upstream end 420a of focusing chamber 420.

Figure 3C:
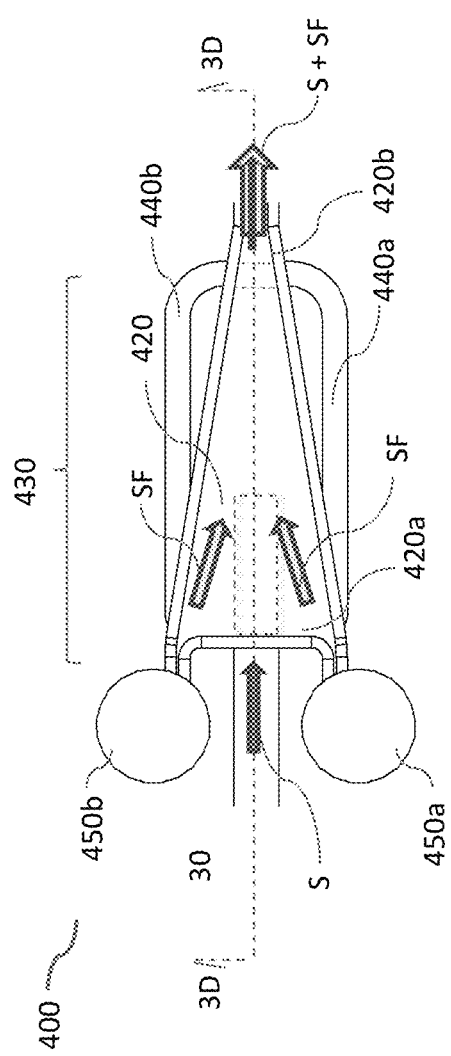
FIG. 3C is top view of a portion of a flow channel geometry in accordance with the embodiment of FIG. 3A.
Figure 3D:
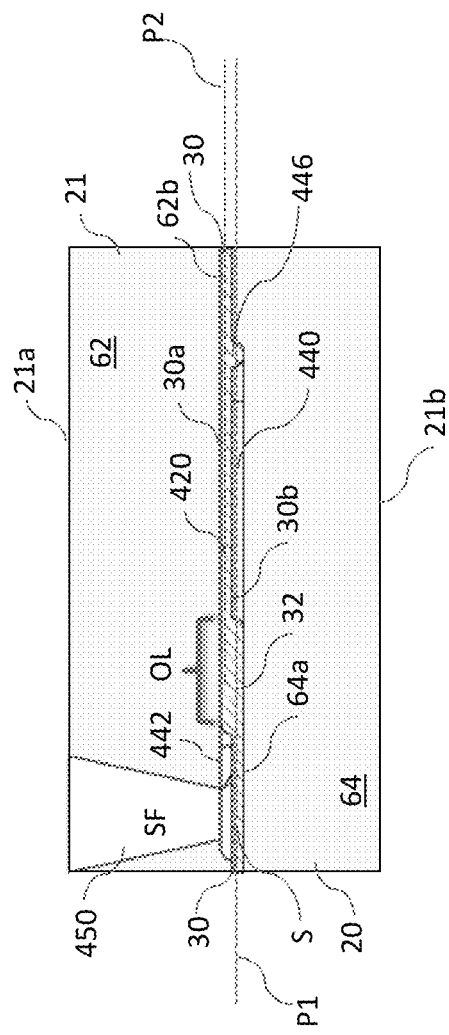
FIG. 3D is a cross-section through line 3D-3D of FIG. 3C of a portion of a flow channel geometry in accordance with the embodiment of FIG. 3A
Figure 3E:
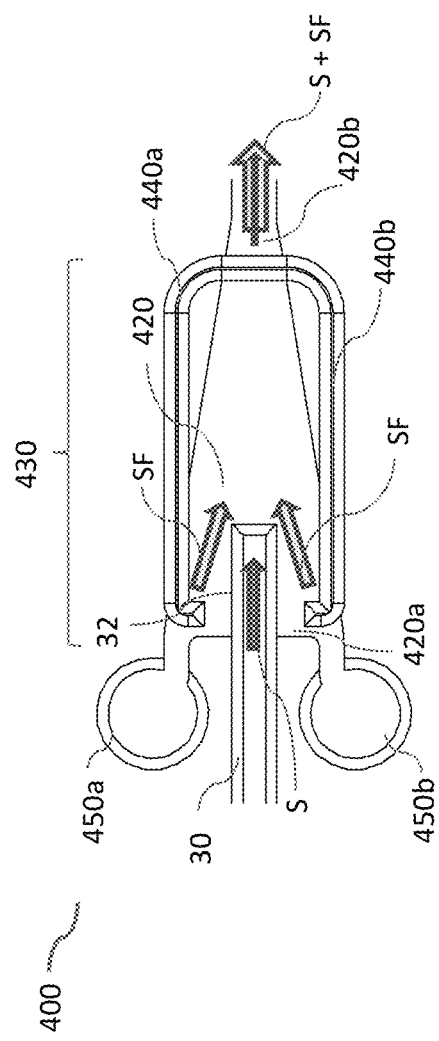
FIG. 3E is bottom view of a portion of a flow channel geometry in accordance with the embodiment of FIG. 3A.

As best shown in FIGS. 3B, 3D and 3E, at the upstream end 420a of focusing chamber 420, a sample inlet portion 32 of the micro channel 30 transporting sample fluid S extends beneath the plane of the lateral fluid focusing chamber 420. The sample inlet portion 32 of micro channel 30 is centered along the longitudinal centerline CL. The sample S is injected into the plane of the focusing chamber 42 through the opening where the sample inlet portion 32 of the micro channel 30 and the lateral fluid focusing chamber 420 overlap OL. As shown in FIG. 3E, the length of the overlap OL is approximately a third of the length of the focusing chamber 420. In other words, the sample inlet portion 32 and the lateral fluid focusing chamber 420 share a common opening (where otherwise they would have shared a common wall). Sample fluid S enters focusing chamber 420 from below via a symmetrically centered opening having a length equal to the overlap OL region and a width equal to the width of micro channel 30. Thus, in this embodiment, the sample stream S jogs from the plane of the upstream micro channel 30 upward into the focusing fluid SF within the plane of the focusing chamber as it is introduced into the focusing chamber.

As the sample stream and the focusing fluid progress along the lateral fluid focusing chamber 420 the lateral dimension of the chamber 420 decreases. As the chamber 420 narrows or tapers in the lateral direction as the fluid travels downstream, an increasing inward force from the lateral sides of the chamber 420 acts on the fluid within the chamber, thus tending to focus (e.g., constrict) the sample S in the middle of the lateral fluid focusing chamber 420. The increasing inward force further tends to accelerate both the sheath and the sample within the fluid focusing region 430 in the flow channel 30.

At the downstream end 420b of the lateral fluid focusing chamber 420, the vertical fluid focusing component provides a vertical upwardly-directed focusing force. Specifically, vertical fluid focusing channels 440a, 440b introduce focusing fluid FS from inlet ports 450a, 450b into the lateral fluid focusing chamber 420 at the downstream end 420b. As best shown in FIGS. 3B, 3D and 3E, the vertical fluid focusing channels 440a, 440b extend under channel 30. Where the top surface of channel 440a intersects the lower surface 30b of channel 30 an opening or aperture forms a vertical focusing flow inlet 446 so that focusing fluid FS from channels 440a, 440b may enter channel 30. Thus, the vertical fluid focusing channels 440a, 440b introduce focusing fluid FS into fluid focusing chamber 420 at vertical focusing flow inlet 446 from below.

Referring now to FIG. 3A, 3B, 3C or 3E, the vertical fluid focusing channels 440a, 440b may comprise a U-shaped or looping channel that branches away from the lateral fluid focusing chamber 420 and is provided in fluid communication at aperture region 446 with the lateral fluid focusing chamber 420 further downstream. In this manner, the vertical fluid focusing channels 440 may provide a means for diverting a portion of sheath fluid that may then be reintroduced into the flow channel 30 at a later point to focus the vertical position of the core stream of sample S.

As best shown in FIGS. 3D and 3E, the sample S enters the fluid focusing region 430 at the upstream end 430a in a plane P1 (see FIG. 3D) below the plane P2 (see FIG. 3D) in which the lateral fluid focusing chamber 420 is located. The sample S is directed upward from plane P1 into the plane P2 of the lateral focusing chamber 420 in the overlapped region OL. Then, at the downstream end 430b of the fluid focusing region 430, the laterally focused sample within a sheath of focusing fluid (S+SF) is vertically focused upward by the introduction of focusing fluid SF at the vertical focusing flow inlet 446 from below. The focused stream exits the fluid focusing region 430 in the P2 (see FIG. 3D) plane.

FIG. 3C is a top view of the core stream forming geometry 400, including fluid focusing region 430 and lateral fluid focusing component 420. A sample flow S is illustrated entering the lateral focusing chamber 420 from the micro channel 30. Focusing fluid flow SF is illustrated entering the lateral fluid focusing chamber 420 from each sheath inlet port 450 at the upstream region 420b of the lateral fluid focusing chamber 420. Further, the focusing fluid SF is introduced into the lateral fluid focusing chamber 420 from a lateral edge. In this particular embodiment, the focusing fluid SF is introduced into the lateral fluid focusing chamber 420 at a lateral, upstream corner of the fluid focusing chamber 420.

The width of the lateral fluid focusing chamber 420 decreases in a downstream direction. In this particular embodiment, the width decreases linearly over a majority of the fluid focusing region 430. The sheath flow SF provides an increasing shearing force on the sample S, both accelerating the flow of the sample S, spacing out particles in the sample, and laterally focusing the sample flow into the center of the lateral fluid focusing chamber 420.

The vertical flow of the sample S is influenced by two features of the core stream forming geometry 400, which can be best seen in FIG. 3D. FIG. 3D represents a vertical cross-section along a longitudinal axis of the core stream forming geometry 400. A first downwards vertical influence on the sample stream is created upon entry into the lateral fluid focusing chamber 420, because the sample is introduced from under the lateral fluid focusing region 420, so that its upward flow will be resisted by the sheath flow SF above it.

A sample flow S enters the core stream forming geometry region via micro channel 30 and via sample inlet portion 32. The sample S reaches the end of the overlapped sample inlet region OL and moves upwards against a sheath flow SF in the plane of the lateral fluid focusing chamber 420. Once the core stream of sample S reaches vertical focusing flow inlet 446, the vertical fluid focusing channels 440*a*, 440*b* introduce focusing fluid SF upward, thereby directing the sample S upwards and focusing the sample S away from the bottom of the flow channel 30.

FIG. 3D demonstrates two notably advantageous concepts. First, the representative sample flow S reflects a non-perpendicular injection point of the sample S, e.g., via the sample inlet portion 32. Thus, in exemplary embodiments, the sample inlet portion 32 of the micro channel 30 may be configured to introduce the sample S in substantially a same flow direction (longitudinally) as the focusing fluid SF. Second, in order to provide enhanced core formation and centering, multiple sheath fluid inlets for introducing focusing fluid SF into fluid focusing region 430 may be provided. For example, in a downstream focusing region 420*b*, vertical fluid focusing channels 440*a*, 440*b* may introduce focusing fluid SF at a vertical focusing flow inlet 446.

The core stream forming geometry 400 accelerates and focuses the sample S and the sheath fluid SF around the centrally introduced sample S. Preferably, the fluid focusing region 430 focuses the sample S away from the sides of the micro channel. The vertically focusing component, joining the micro channel 30 downstream of the fluid focusing region 430, provides additional focusing of the sample S within the focusing fluid SF. In the embodiment of FIG. 3A-3E, this secondary focusing focuses the sample in a vertical direction from below the sample S. The combination of the lateral focusing and the vertical focusing provides three-dimensional focusing of the sheath fluid around the sample. Advantageously, the resulting flow is hydrodynamically focused on all sides of the sample S away from the walls of the flow channel 30, with the sample S being suspended as a focused core in the approximate center of the channel 30.

After being focused in the focusing region 430, the sample may continue through an inspection region and a particle diverting and/or sorting region. Further, the particles may be aligned and/or oriented according to specific features in the following description and a sort action may be performed according to various mechanisms.

FIGS. 4A-4D, 5A-5D and 6A-6D introduce various embodiments which include additional focusing regions, e.g., tertiary focusing regions, downstream of the secondary focusing regions.

Figure 4A:
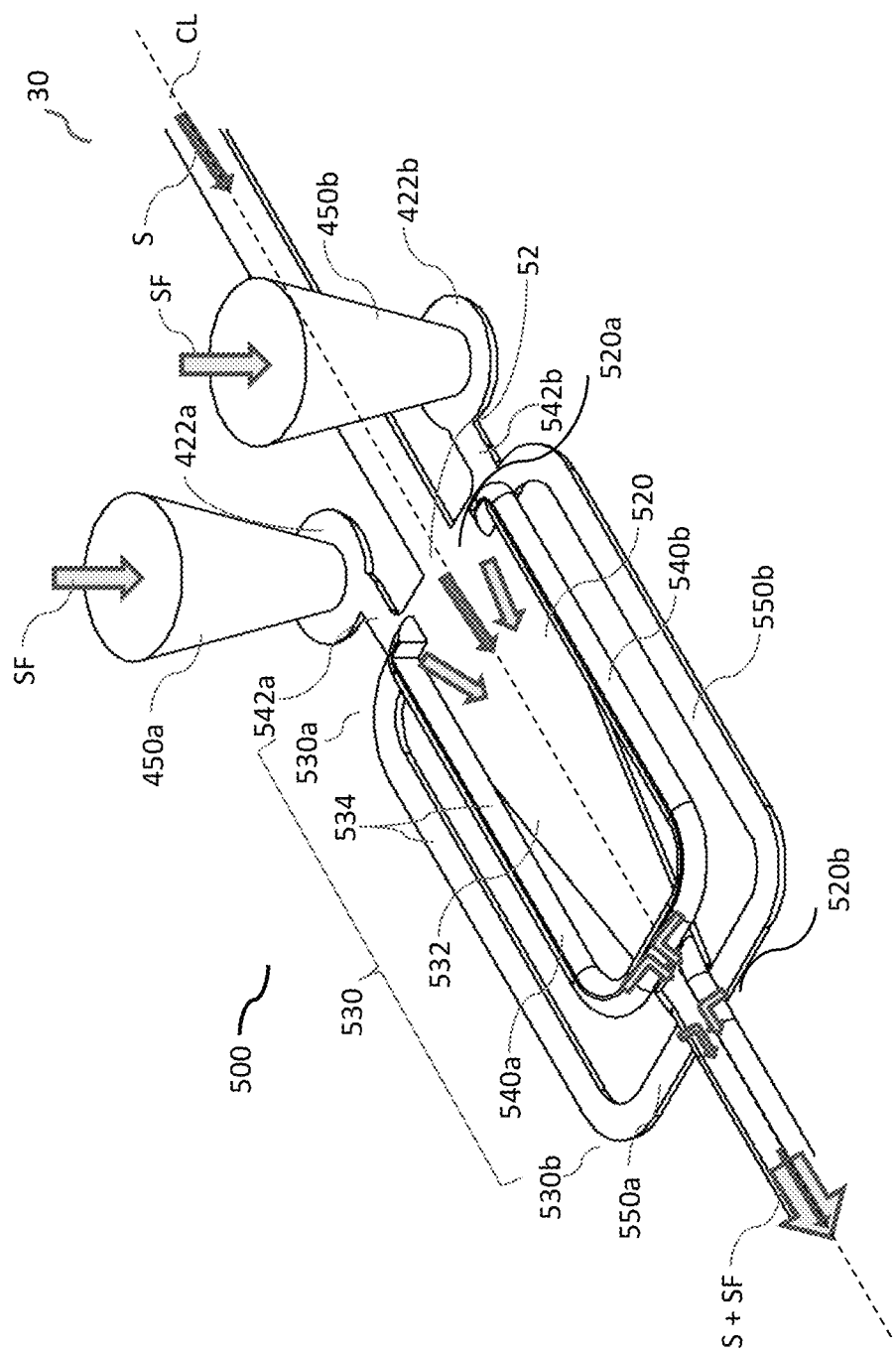
FIG. 4A is a top perspective view of a portion of a flow channel geometry with arrows schematically depicting flow of sample fluid and focusing fluid in accordance with certain embodiments described herein.
Figure 4C:
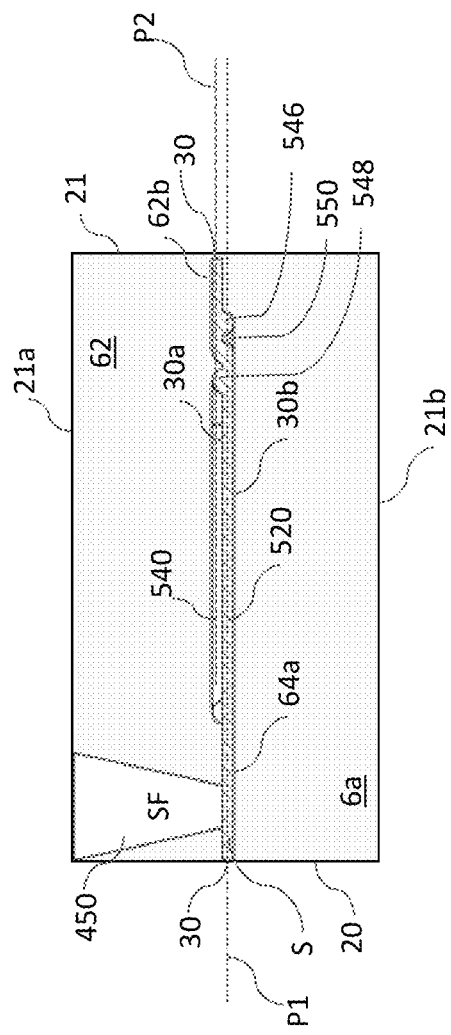
FIG. 4C is a cross-section through line 4C-4C of FIG. 4B of a portion of a flow channel geometry in accordance with the embodiment of FIG. 4A.
Figure 4D:
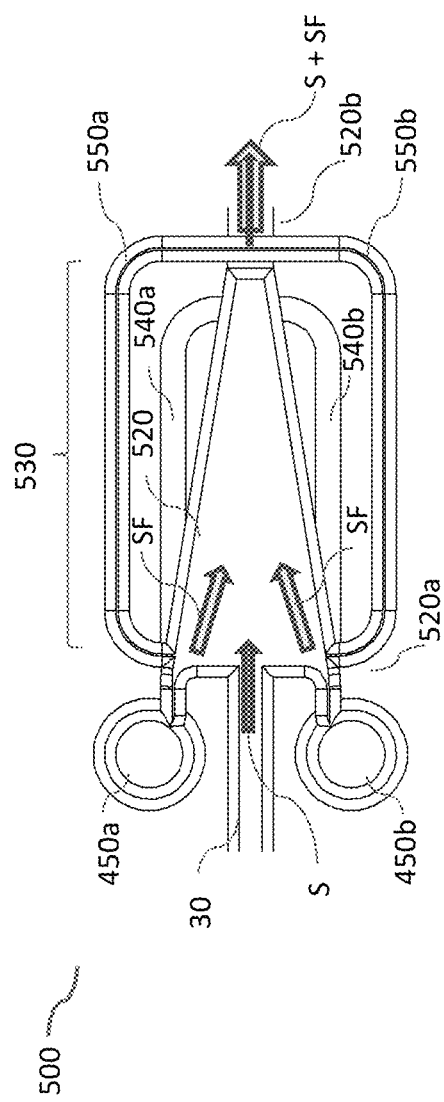
FIG. 4D is bottom view of a portion of a flow channel geometry in accordance with the embodiment of FIG. 4A.
Figure 5A:
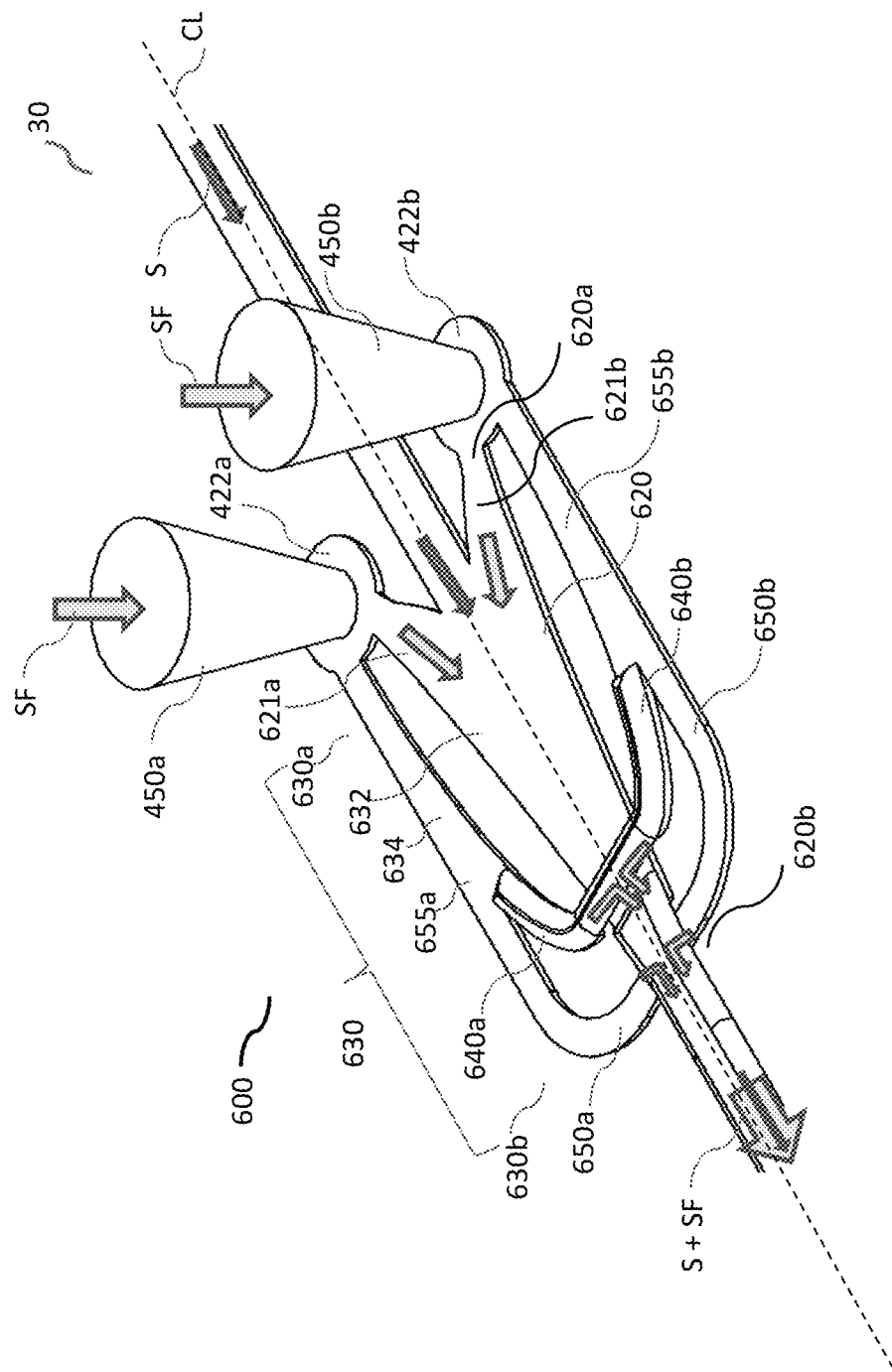
FIG. 5A is a top perspective view of a portion of a flow channel geometry with arrows schematically depicting flow of sample fluid and focusing fluid in accordance with certain embodiments described herein.
Figure 5B:
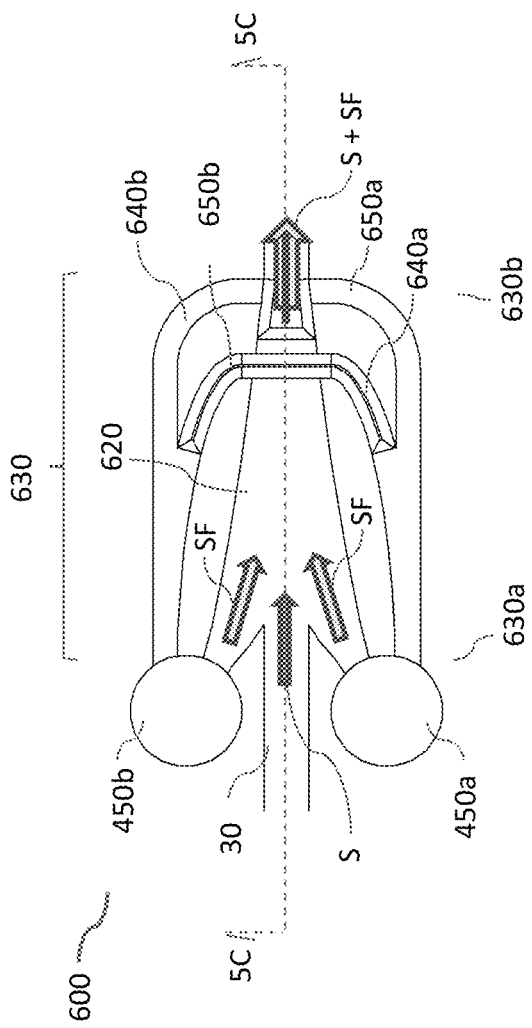
FIG. 5B is top view of a portion of a flow channel geometry in accordance with the embodiment of FIG. 5A.
Figure 5C:
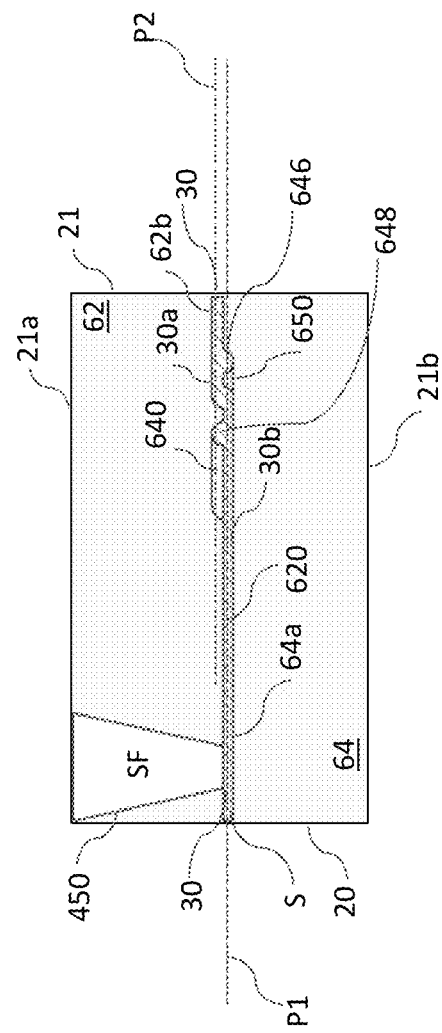
FIG. 5C is a cross-section through line 5C-5C of FIG. 5B of a portion of a flow channel geometry in accordance with the embodiment of FIG. 5A.
Figure 5D:
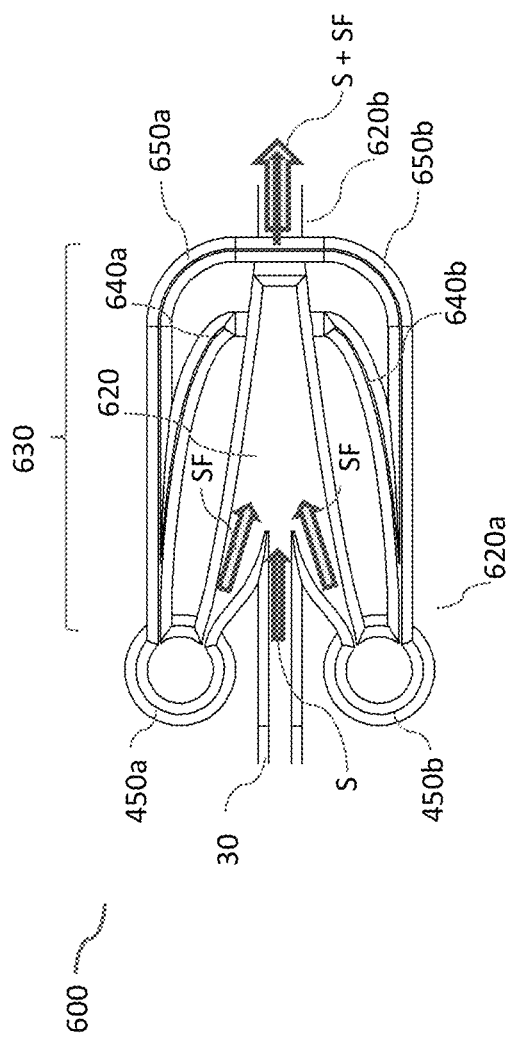
FIG. 5D is bottom view of a portion of a flow channel geometry in accordance with the embodiment of FIG. 5A.

Turning to FIGS. 4A-4D, an alternative core stream forming geometry 500 is illustrated which incorporates a fluid focusing region 530. Fluid focusing region 530 includes a vertical fluid focusing component 534 configured as a double horseshoe or double loop an including first and second sets of vertical fluid focusing channels 540, 550. This embodiment relates to a core stream forming geometry 500 having a first pair of vertical fluid focusing channel 540*a*, 540*b* and second pair of vertical fluid focusing channel 550*a*, 550*b* configured to introduce opposing vertical fluid focusing sheath flows into lateral fluid focusing chamber 520 for an improved core stream formation. Specifically, as best shown in FIGS. 4A and 4C, the first pair of vertical fluid focusing channel 540*a*, 540*b* introduces focusing fluid SF into the downstream end 520*b* of fluid focusing chamber 520 at vertical focusing flow inlet 548 (see FIG. 4C) from above. The second pair of vertical fluid focusing channel 550*a*, 550*b* introduces focusing fluid SF into the downstream end 520*b* of fluid focusing chamber 520 at vertical focusing flow inlet 546 (see FIG. 4C) from below. Vertical focusing flow inlet 548 is located upstream of vertical focusing flow inlet 546. Thus, after being laterally focused, the stream is vertically focused downward and then vertically focused upward.

FIGS. 4A and 4C show that a sample inlet 52 (see FIG. 4A) of the micro channel 30 is positioned at the same vertical plane as the lateral fluid focusing chamber 520. Further, the lateral fluid focusing chamber 520, the vertical fluid focusing channels 550*a*, 550*b*, and the sample inlet 52 all lie in the same plane, plane P1 (see FIG. 4C). Additionally, vertical fluid focusing channels 540*a*, 540*b* lie in a plane P2 (see FIG. 4C) above plane P1 (see FIG. 4C). After being subjected to the laterally-directed focusing features of the lateral focusing chamber 520, the vertical focusing channels 540*a*, 540*b* and the vertical focusing channels 550*a*, 550*b* introduce opposing vertical focusing forces (via vertical focusing flow inlets 548, 546, respectively) that act on the sample S. The focused stream exits the fluid focusing region 530 in the P2 plane. Advantageously, a more focused and/or aligned sample core stream may result.

Referring to FIG. 4A, fluid focusing region 530 includes a lateral fluid focusing component 532 which includes lateral fluid focusing chamber 520. Similar to the embodiment of FIGS. 3A-3E, the lateral fluid focusing chamber 520 is widest at its upstream end 520*a* and narrowest at its downstream end 520*b*. Between the upstream end 520*a* and the downstream end 520*b*, the chamber 520 substantially linearly tapers symmetrically with respect to the centerline CL in the lateral direction. Between the upstream end 520*a* and the downstream end 520*b*, the chamber 520 has a substantially constant thickness. Further, the upstream end 520*a* is provided as a substantially flat wall having two openings, one at each corner, for admitting focusing fluid SF.

Thus, as illustrated, two sheath inlet ports 450*a*, 450*b* may symmetrically introduce focusing fluid SF into the lateral fluid focusing chamber 520. Referring to FIG. 4A, a relatively short channel 542*a* extends between the sheath aggregating volume 422*a* and the corner opening of the lateral fluid focusing chamber 520. Similarly, a relatively short channel 542*b* extends between the sheath aggregating volume 422*b* and laterally opposed corner opening of the lateral fluid focusing chamber 520. Thus, focusing fluid SF enters chamber 520 from opposed lateral edges (or lateral sides) of the upstream end 520*a* of focusing chamber 520.

In contrast to the embodiment of FIGS. 3A-3E and as best shown in FIG. 4C, at the upstream end 520*a* of focusing chamber 520, sample fluid S directly flows into the chamber 520, in the same plane P1 in which the chamber 520 is located, via a sample inlet 52 (see FIG. 4A) of the micro channel 30.

Referring to FIG. 4B, focusing fluid SF flows into lateral fluid focusing chamber 520 from sheath inlet ports 450. The focusing fluid SF from each inlet port 450 may be divided into three sheath flow portions. A first focusing fluid portion may enter the lateral fluid focusing chamber 520 at its upstream corners. In response to the narrowing lateral width of the lateral fluid focusing chamber 520, the focusing fluid SF tends to focus the sample S in the center of the lateral fluid focusing channel 520. A second focusing fluid portion from each inlet port 450 may be diverted through a vertical fluid focusing channel 550*a* (or 550*b*) and a third focusing fluid portion may be directed through a vertical fluid focusing channel 540*a* (or 540*b*).

In this embodiment, the sheath aggregating volume 522 may advantageously provide a greater cross sectional area than the end of the conical sheath inlet 450, thus providing a beneficial volume for distributing focusing fluid at relatively high sheath flow rates through each of the sheath flow portions. Further, the length the vertical focusing channels 540*a*, 540*b* is less than the length of vertical focusing channels 550*a*, 550*b*. The shorter length of vertical focusing channels 540*a*, 540*b* means that these channels have less resistance to flow of the focusing fluid therethrough (as compared to the vertical focusing channels 550*a*, 550*b*). Thus, the volume of focusing fluid that may be introduced into the fluid focusing region 530 at vertical focusing flow inlet 548 may be greater than the volume of focusing fluid that may be introduced into the fluid focusing region 530 at vertical focusing flow inlet 546. The relative lengths of the vertical focusing channels 540, 550 may be modified in order control the vertical focusing of the stream. In particular a difference in the focusing fluid flow through the first set of vertical focusing channels 540 and the second set of vertical focusing channels 550 may provide for an improved ability to focus the vertical position of a core stream in a flow channel 30. In general, it may be desirable to maintain a balance between the vertical focusing forces at the vertical focusing flow inlet 548 and the vertical focusing flow inlet 546.

Turning now to FIG. 4C, a vertical cross-section along a longitudinal axis of the core stream forming geometry 500 illustrates a core stream of sample S and a focusing fluid SF introduced into the flow channel 30 at substantially the same vertical position. Focusing fluid SF from the first set of vertical fluid focusing channels 540 provides a downward focusing influence on the core stream of sample S, followed by an upward focusing influence from sheath fluid provided from the second set of vertical fluid focusing channels 550. The portion of the flow channel 30 following the opposing vertical sheath flows is at an elevated vertical position relative to the lateral fluid focusing chamber 520 and the sample inlet 52. The portion of the flow channel 30 following the focusing region may be further manipulated in a region designed to impart orientation to particles in the core stream of sample.

FIGS. 5A-5D illustrate an alternative embodiment of the core stream forming geometry 600 having substantially the same vertical cross section as the embodiment of FIGS. 4A-4D (compare FIG. 4C with FIG. 4C). There may be certain efficiencies gained in several stream lined aspects relating to the sheath fluid flow paths illustrated in FIGS. 5A-5D. In one aspect sheath fluid passes through from each sheath aggregating volume 422 into a tapered focused inlet 632 which immediately puts the focusing fluid into a trajectory for laterally focusing the core stream of sample fluid S. The tapered inlets 621*a*, 621*b* may eliminate any fluid dead zone which may be caused by blunt entry geometries.

Further, the tapered inlets 621 advantageously are configured to allow the focusing fluid SF to travel in an expanding inlet channel that so that the focusing fluid is travelling substantially parallel (or at a slight angle) to the sample fluid S flowing in the micro channel 30 immediately prior to the tapered inlets 621 merging with the channel 30. This angle may be less than 45 degrees from the longitudinal axis of the micro channel 30. In preferred embodiments, this angle may be less than 30 degrees, less than 25 degrees, and even less than 20 degrees. The inlets 621 may expand to the point of merger with the micro channel 30. The configuration of the inlets 621 provides a focusing fluid flow trajectory that may be substantially aligned with the sample fluid flow. Notably, enabling the focusing fluid SF to expand and travel substantially parallel to the sample S prior to merging allows a laminar flow region to be established where all of the fluid is travelling in parallel as the fluids are merged. This streamlined merging may provide a substantial reduction in fluid mixing and turbulence at the point of merger.

Further, the tapered inlets 621 allow the lateral fluid focusing component 632 and the vertical fluid focusing component 634 to be somewhat isolated from each other. In particular, the upstream end of the vertical fluid focusing component is upstream of where sample S enters the fluid focusing chamber 620, thus mitigating any potential for sample S to inadvertently flow in the vertical fluid focusing component 634.

In this particular embodiment, the lateral fluid focusing chamber 620 has slightly convexly curved lateral edges.

Each of the first set of vertical fluid focusing channels 640 and the second vertical fluid focusing channels 650 are also streamlined with a common inlet 655. However, in contrast to the embodiment of FIGS. 4A-4D, in this embodiment, the cross-sectional areas of the vertical focusing channels 650, 640 need not be constant along their length, but may vary from one portion to another. Further, the cross-sectional area of vertical fluid focusing channels 640 may be larger than the flatter cross-section area of vertical fluid focusing channels 650. This larger cross-sectional area of vertical fluid focusing channels 640 relative to the flatter cross section of vertical fluid focusing channels 650 may allow a greater flow of vertical focusing fluid to enter chamber 620 at vertical focusing flow inlet 648 (see FIG. 5C) than at vertical focusing flow inlet 646 (see FIG. 5C).

The greater cross-sectional area and the shorter length of vertical focusing channels 640*a*, 640*b* mean that these channels have less resistance to flow of the focusing fluid therethrough (as compared to the vertical focusing channels 650*a*, 650*b*). Thus, the volume of focusing fluid that may be introduced into the fluid focusing region 630 at vertical focusing flow inlet 648 may be greater than the volume of focusing fluid that may be introduced into the fluid focusing region 630 at vertical focusing flow inlet 646. The relative cross-sectional areas and/or the relative lengths of the vertical focusing channels 640, 650 may be modified in order control the vertical focusing of the stream. In some aspects, it may be desirable to maintain a balance between the vertical focusing forces at the vertical focusing flow inlet 548 and the vertical focusing flow inlet 546. Thus, providing varying lengths, cross-sectional areas and/or non-constant cross-sectional areas for the different vertical fluid focusing channels may allow the vertical focusing forces to be balanced.

Thus, advantageously, aspects disclosed herein allow the designer to tailor the focusing flows acting on the stream so as to optimize the position and/or shape of the focused stream within the channel.

Figure 6A:
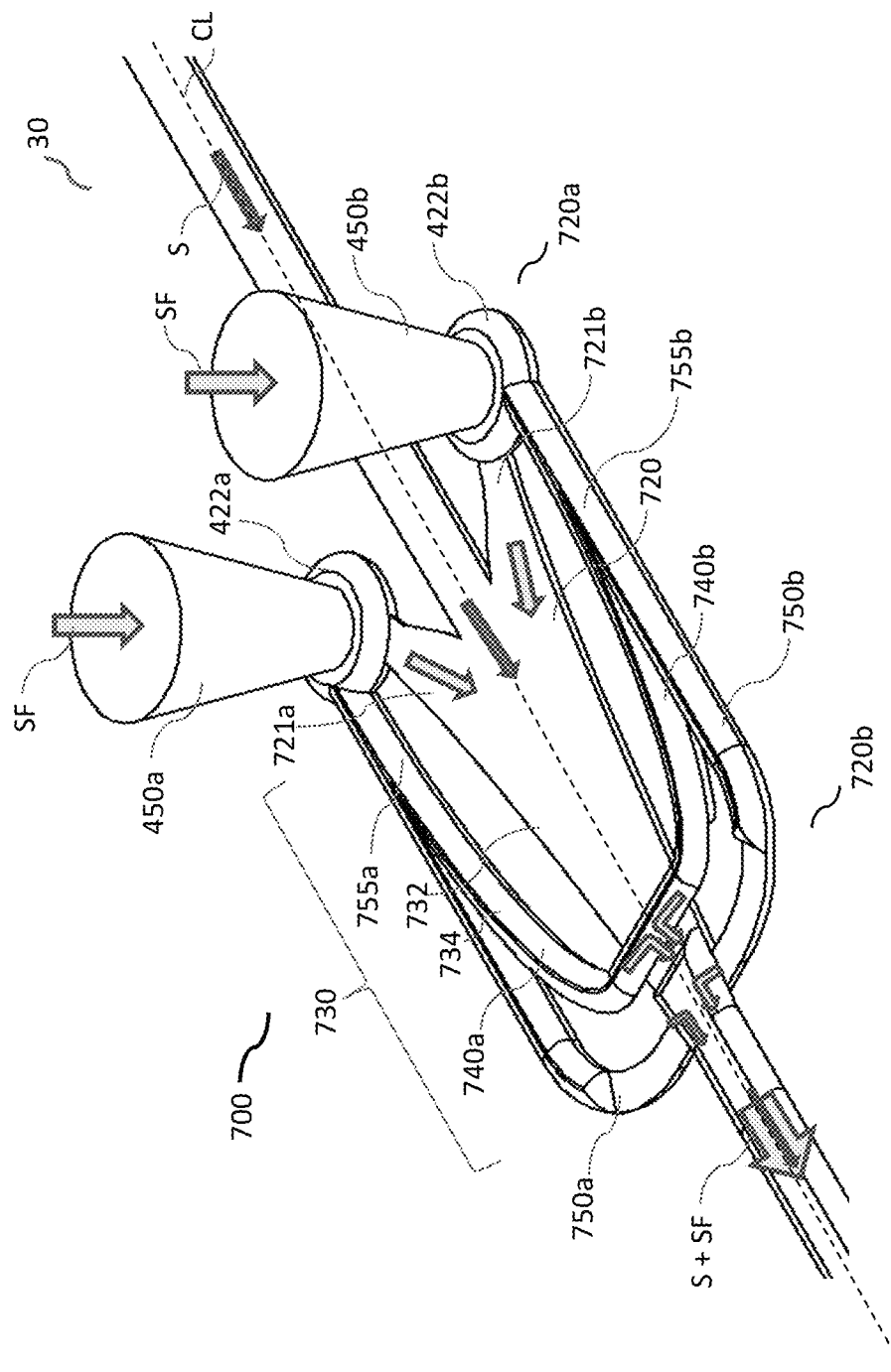
FIG. 6A is a top perspective view of a portion of a flow channel geometry with arrows schematically depicting flow of sample fluid and focusing fluid in accordance with certain embodiments described herein.
Figure 6C:
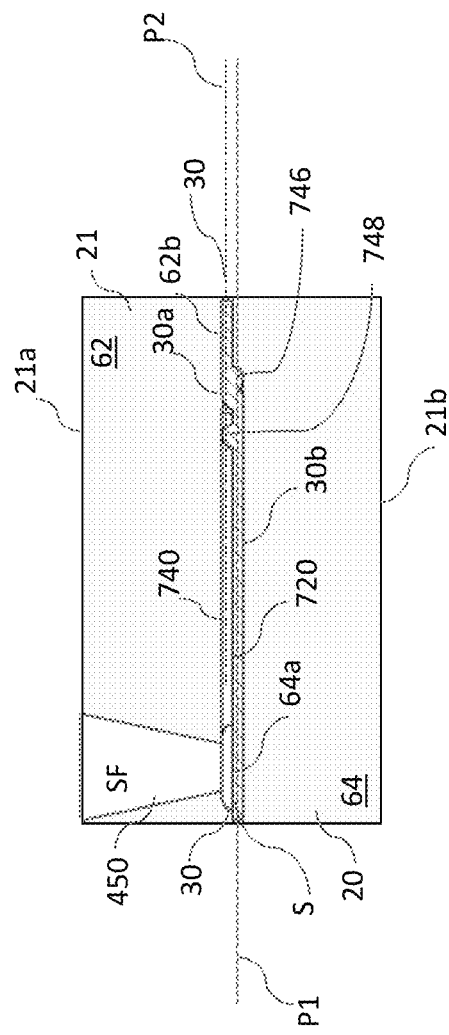
FIG. 6C is a cross-section through line 6C-6C of FIG. 6B of a portion of a flow channel geometry in accordance with the embodiment of FIG. 6A.
Figure 6D:
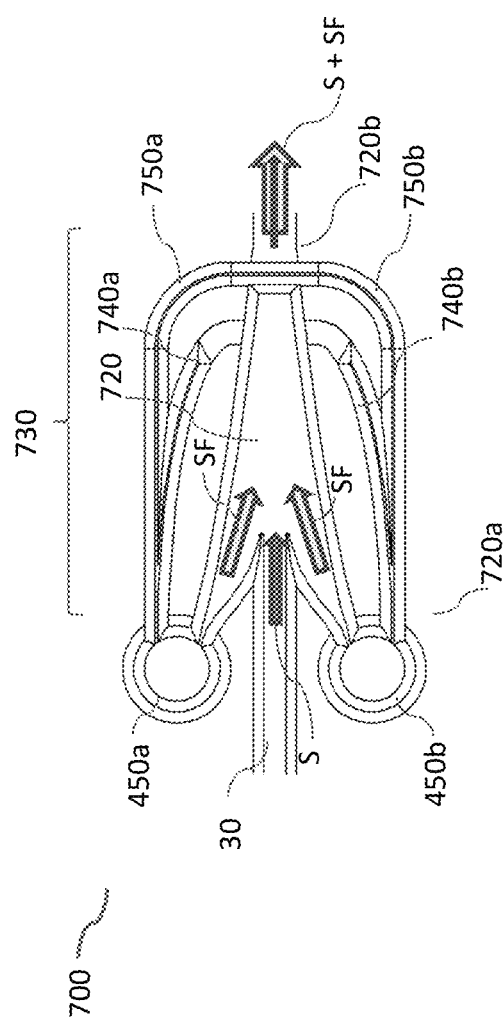
FIG. 6D is bottom view of a portion of a flow channel geometry in accordance with the embodiment of FIG. 6A.

FIGS. 6A-6D illustrate another embodiment of the core stream forming geometry 700. Similar to the embodiment of FIGS. 5A-5D and as best shown in FIG. 6A, this embodiment also has streamlined fluid focusing flow components, such as a dedicated tapered inlet 721 extending into the lateral fluid focusing chamber 720 from the inlet port 450 and a common focusing fluid channel 755 connected directly to the sheath aggregating volume 422 of each sheath inlet 450 and supplying focusing fluid SF to the first and second sets of vertical fluid focusing channels 740, 750. Additionally, FIGS. 6A-6D illustrate an alternative vertical placement of some portions of each of the first vertical fluid focusing channel 740 and the second vertical fluid focusing channel 750.

Further, compared to the embodiment of FIGS. 5A-5D, the embodiment of FIGS. 6A-6D are provided with a relatively large cross sectional areas of both the first set of vertical fluid focusing channels 740 and the second set of vertical fluid focusing channels 750. This greater cross-sectional area provides less resistance to the focusing fluid entering the vertical fluid focusing component 734 relative to the focusing fluid enter the lateral fluid focusing component 732. Thus, another way to balance and/or control the focusing forces acting on the sample S is provided by controlling the relative fluidic resistances of the focusing fluid flow into the vertical fluid focusing component 734 and into the lateral fluid focusing component 732.

Even further, the embodiment of FIGS. 6A-6D are provided with an enhanced sheath aggregating volume 422 in other to accommodate the relatively large cross sectional areas of both the first set of vertical fluid focusing channels 740 and the second set of vertical fluid focusing channels 750. Also of interest is that the vertical fluid focusing channels 740, 750 are configured with a reduced downstream cross-sectional area (as compared to the greater cross-sectional area provided in the upstream portion of the channels).

Figure 7C:
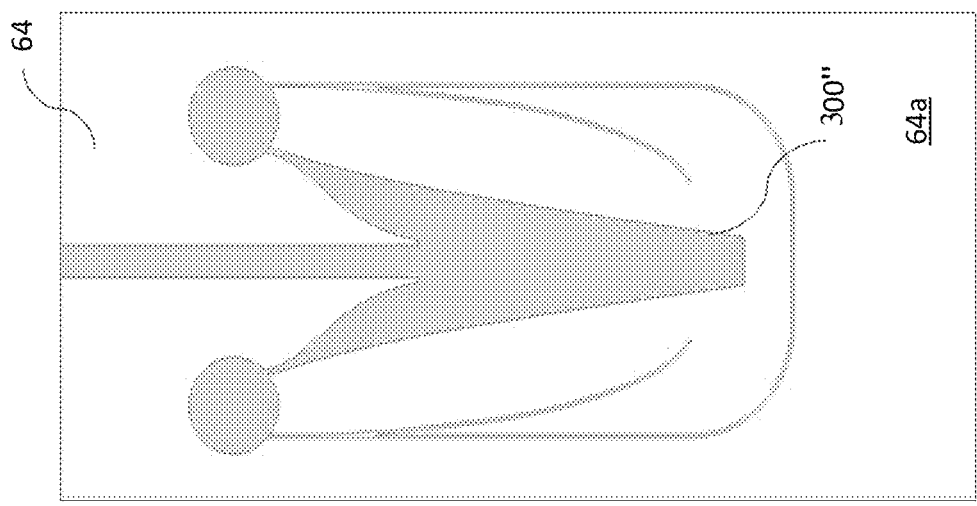
FIG. 7C is top view of a portion of a lower substrate layer in accordance with the embodiment of FIGS. 5A and 7A, schematically illustrating the micro channel geometry formed in the upper surface of the lower substrate layer.
Figure 7B:
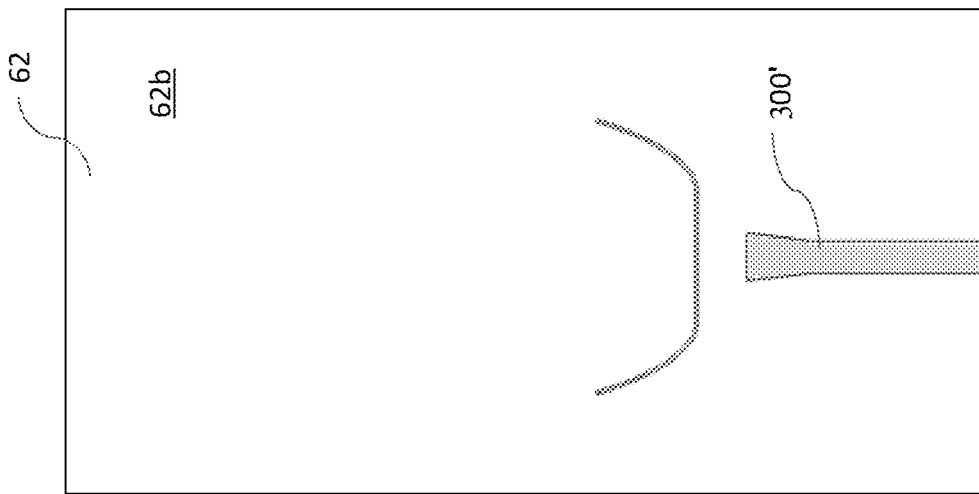
FIG. 7B is bottom view of a portion of an upper substrate layer in accordance with the embodiment of FIGS. 5A and 7A, schematically illustrating the micro channel geometry formed in the lower surface of the upper substrate layer.
Figure 7A:
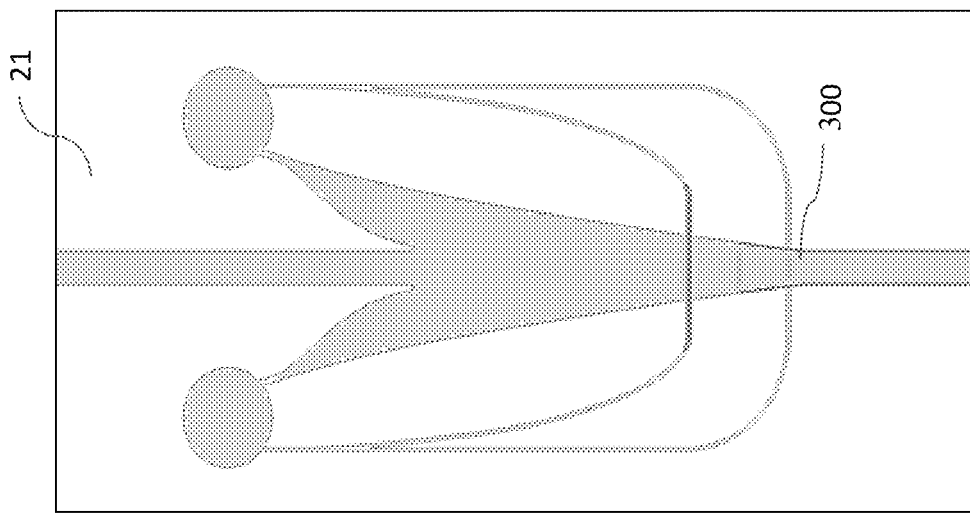
FIG. 7A is top view of a portion of a substrate of the microfluidic chip, schematically illustrating micro channel geometry, in accordance with the embodiment of FIG. 5A, formed between an upper substrate layer and a lower substrate layer.

Referring back to FIG. 2 and also to FIGS. 3D, 4C, 5C and 6C, according to certain embodiments, substrate 21 may be formed by bonding or otherwise attaching an upper substrate layer 62 to a lower substrate layer 64. Referring now to FIG. 7A, a top view of the substrate 21 is shown with the core stream forming geometry 300 visible through the top layer of the substrate. FIG. 7B, a lower surface 62b of the upper substrate 62 of the substrate of FIG. 7A is shown. Portions of the fluid focusing components 300' of the core stream forming geometry 300 are shown provided in the lower surface 62b. In FIG. 7B, a lower surface 62b of the upper substrate 62 of the substrate of FIG. 7A is shown. Complementary portions of the fluid focusing components 300" core stream forming geometry 300 are shown provided in the lower surface 62b. In FIG. 7C, an upper surface 64a of the lower substrate 64 of the substrate of FIG. 7A is shown. Portions of the fluid focusing components are shown provided in the upper surface 64a. The portions of the fluid focusing components 300', 300" provided in these substrate layer surfaces may be provided (via additive or subtractive manufacturing). When the upper surface 64a and the lower surface 62b are assembled together with the complementary portions of the fluid focusing components aligned with each other, the complete core stream forming geometry is formed. Thus, a complicated core stream forming geometry 300 such as the exemplary core stream forming geometries described herein, may be simply and efficiently provided with just two substrate layers. While the core stream forming geometry 300 depicted in the embodiment in FIGS. 7A-C is illustrated as the exemplary core stream forming geometry 600 of the embodiment of FIGS. 5A-D, it is appreciated that an upper substrate layer 62 and a lower substrate layer 64 may similarly be used to define any number of different stream forming geometries including, for example, any of the exemplary stream forming geometries 400, 500, 600 and 700 described herein, for example, with respect to the embodiments of FIGS. 3A-E, 4A-D, 5A-D and 6A-D.

As can be understood from the foregoing, features described for focusing a core stream may be combined with various features for monitoring, detecting, analyzing, and/or sorting particles of interest. See, e.g., U.S. Pat. Nos. 6,877,528, 6,808,075, and 7,298,478, which are hereby incorporated by reference in their entireties.

A system and method for producing a focused sample in a flow channel, such as a micro channel, has been described herein. As can be easily understood from the foregoing, the basic concepts of the present disclosure may be embodied in a variety of ways. As such, the particular embodiments or elements disclosed by the description or shown in the figures accompanying this application are not intended to be limiting, but rather illustrative of the numerous and varied embodiments generically encompassed by the present disclosure or equivalents encompassed with respect to any particular element thereof. In addition, the specific description of a single embodiment or element may not explicitly describe all embodiments or elements possible; many alternatives are implicitly disclosed by the description and figures.

Moreover, for the purposes of the present disclosure, the term "a" or "an" entity refers to one or more of that entity. As such, the terms "a" or "an", "one or more" and "at least one" can be used interchangeably herein.

All numeric values herein are assumed to be modified by the term "about", whether or not explicitly indicated. For the purposes of the present invention, ranges may be expressed as from "about" one particular value to "about" another particular value. It will be understood that the endpoints of each of the ranges are significant both in relation to the other endpoint, and independently of the other endpoint. When a value is expressed as an approximation by use of the antecedent "about," it will be understood that the particular value forms another embodiment.

We claim:

1. A microfluidic assembly for use with a particle processing instrument, the microfluidic assembly comprising:
   a substrate; and
   a flow channel formed in the substrate, the flow channel having:
      an inlet configured to receive a sample stream;
      a fluid focusing region configured to focus the sample stream, the fluid focusing region having a lateral fluid focusing feature, a first vertical fluid focusing feature, and a second vertical fluid focusing feature, the lateral, the first vertical, and the second vertical fluid focusing features provided at different longitudinal locations along the flow channel, wherein a bottom surface of the flow channel lies in a first plane upstream of the first and second vertical fluid focusing features and the bottom surface of the flow channel shifts vertically upward to lie in a second plane downstream of the first and second vertical focusing features; and
      an inspection region at least partially downstream of the fluid focusing region.

2. The microfluidic assembly of claim 1, wherein the lateral fluid focusing feature is configured to introduce focusing fluid into the flow channel symmetrically with respect to a centerline of the sample stream.

3. The microfluidic assembly of claim 2, wherein the first and second vertical fluid focusing features are located downstream of the lateral fluid focusing feature;
  wherein the first vertical fluid focusing feature includes a first vertical fluid focusing aperture configured to introduce focusing fluid into the flow channel from above the sample stream; and
  wherein the second vertical fluid focusing feature includes a second vertical fluid focusing aperture configured to introduce focusing fluid into the flow channel from below the sample stream.

4. The microfluidic assembly of claim 3, wherein the first vertical fluid focusing aperture is in fluid communication with a first vertical fluid focusing channel and the second vertical fluid focusing aperture is in fluid communication with a second vertical fluid focusing channel.

5. The microfluidic assembly of claim 3, wherein the first vertical fluid focusing aperture is in fluid communication with a first pair of fluid focusing channels;
  wherein the second vertical fluid focusing aperture is in fluid communication with a second pair of fluid focusing channels; and
  wherein each of the first pair and the second pair of fluid focusing channels are symmetrically arranged with respect to a centerline of the flow channel.

6. The microfluidic assembly of claim 1, wherein the sample stream and the focusing fluid associated with the lateral fluid focusing feature enter the fluid focusing region in a same plane.

7. The microfluidic assembly of claim 1, wherein the fluid focusing region has a varying width upstream of the first and second vertical focusing fluid features; and
  wherein the flow channel has a constant width between the first and second vertical focusing fluid features and the inspection region.

8. The microfluidic assembly of claim 1, wherein within the fluid focusing region the fluid flow channel transitions from a first cross section shape to a second cross section shape different from the first cross section shape.

9. The microfluidic assembly of claim 1, wherein each of the fluid focusing features is in fluid communication with a first focusing fluid inlet port provided on a top surface of the substrate.

10. The microfluidic assembly of claim 1, wherein each of the fluid focusing features is in fluid communication with a pair of focusing fluid inlet ports provided on a top surface of the substrate.

11. The microfluidic assembly of claim 1, wherein each of the fluid focusing features introduces a focusing fluid into the flow channel at the different longitudinal locations along the flow channel.

12. A microfluidic chip comprising:
  a substantially planar chip substrate having an upper surface and a lower surface;
  a microfluidic flow channel provided within the chip substrate;
  a first inlet port formed on the upper surface of the chip substrate for receiving a focusing fluid;
  wherein the first inlet port is in fluid communication with the microfluidic flow channel,
  wherein the microfluidic flow channel includes a first focusing fluid inlet configured to introduce focusing fluid from the first inlet port into the microfluidic channel in a first direction, a second focusing fluid inlet configured to introduce focusing fluid from the first inlet port into the microfluidic channel in a second direction, and a third focusing fluid inlet configured to introduce focusing fluid from the first inlet port into the microfluidic channel in a third direction,
  wherein the microfluidic flow channel includes a fluid flow focusing region having an upstream end region and a downstream end region,
  wherein the first focusing fluid inlet is configured to introduce focusing fluid into the fluid flow focusing region in the upstream end region,
  wherein the second and third focusing fluid inlets are configured to introduce focusing fluid into the fluid flow focusing region in the downstream end region, and
  wherein a bottom surface of the microfluidic flow channel lies in a first plane upstream of the second and third focusing fluid inlets and the bottom surface of the microfluidic flow channel lies in a second plane downstream of the second and third focusing fluid inlets.

13. The microfluidic chip of claim 12, further comprising:
  a second inlet port formed on the upper surface of the chip substrate for receiving a focusing fluid;
  wherein the second inlet port is in fluid communication with the microfluidic flow channel, and
  wherein the microfluidic flow channel includes a fourth focusing fluid inlet configured to introduce focusing fluid from the second inlet port into the microfluidic channel in a fourth direction,
  wherein the second focusing fluid inlet is configured to introduce focusing fluid from the second inlet port into the microfluidic channel in the second direction, and
  wherein the third focusing fluid inlet is configured to introduce focusing fluid from the second inlet port into the microfluidic channel in the third direction.

14. The microfluidic chip of claim 13, wherein the first and fourth focusing fluid inlets are opposed to each other.

15. The microfluidic chip of claim 12, wherein the microfluidic channel lies in a first plane upstream of the second focusing fluid inlet and lies in a second plane downstream of the third focusing fluid inlet.

16. The microfluidic chip of claim 15, wherein the microfluidic channel is formed when a lower surface of an upper substrate layer and an upper surface of a lower substrate layer are directly joined together.

17. A microfluidic chip comprising:
  a substantially planar substrate having an upper surface and a lower surface;
  a microfluidic channel formed in the substantially planar substrate and having an upper surface and a lower surface;
  an inlet port formed on the upper surface of the substantially planar substrate and configured to receive a focusing fluid;
  a first focusing fluid channel in fluid communication with the inlet port and configured to introduce focusing fluid into the microfluidic channel via a first aperture in the upper surface of the microfluidic channel; and
  a second focusing fluid channel in fluid communication with the inlet port and configured to introduce focusing fluid into the microfluidic channel via a second aperture in the lower surface of the microfluidic channel,
  wherein a bottom surface of the microfluidic channel lies in a first plane upstream of the first aperture and the bottom surface of the microfluidic channel lies in a second plane downstream of the second aperture.

18. The microfluidic chip of claim 17, wherein the microfluidic channel and the first and second focusing fluid channels are formed when a lower surface of an upper substrate layer and an upper surface of a lower substrate layer are directly joined together.

19. The microfluidic chip of claim 17, further comprising:
at least one outlet port formed on the upper surface of the substantially planar substrate and in fluid communication with the fluid flow focusing region.

20. The microfluidic chip of claim 17, wherein the first and second focusing fluid channels are located to a first side of a centerline of the microfluidic channel.

21. The microfluidic chip of claim 17, further comprising a third focusing fluid channel in fluid communication with the inlet port and configured to introduce focusing fluid into the microfluidic channel.

22. A microfluidic assembly for use with a particle processing instrument, the microfluidic assembly comprising:
a substrate; and
a flow channel formed in the substrate, the flow channel having:
an inlet configured to receive a sample stream; and
a fluid focusing region configured to focus the sample stream, the fluid focusing region having a lateral fluid focusing feature, a first vertical fluid focusing feature, and a second vertical fluid focusing feature, the lateral, the first vertical, and the second vertical fluid focusing features provided at different longitudinal locations along the flow channel, wherein a top surface of the flow channel lies in a first plane upstream of the first and second vertical fluid focusing features and the top surface of the flow channel shifts vertically upward to lie in a second plane downstream of the first and second vertical focusing features.

23. The microfluidic assembly of claim 22, wherein the lateral fluid focusing feature is configured to introduce focusing fluid into the flow channel symmetrically with respect to a centerline of the sample stream.

* * * * *

(12) INTER PARTES REVIEW CERTIFICATE (3551st)

United States Patent
Sharpe et al.

(10) Number: US 10,583,439 K1
(45) Certificate Issued: Apr. 8, 2024

(54) HYDRODYNAMIC FOCUSING APPARATUS AND METHODS

(71) Applicants: Johnathan Charles Sharpe; Blair D. Morad; Erin Koksal; Kristopher Scott Buchanan

(72) Inventors: Johnathan Charles Sharpe; Blair D. Morad; Erin Koksal; Kristopher Scott Buchanan

(73) Assignee: CYTONOME/ST, LLC

Trial Number:

IPR2021-00088 filed Oct. 26, 2020

Inter Partes Review Certificate for:

Patent No.: 10,583,439
Issued: Mar. 10, 2020
Appl. No.: 14/213,800
Filed: Mar. 14, 2014

The results of IPR2021-00088 are reflected in this inter partes review certificate under 35 U.S.C. 318(b).

INTER PARTES REVIEW CERTIFICATE
U.S. Patent 10,583,439 K1
Trial No. IPR2021-00088
Certificate Issued Apr. 8, 2024

AS A RESULT OF THE INTER PARTES REVIEW PROCEEDING, IT HAS BEEN DETERMINED THAT:

Claims 1 and 8 are cancelled.

\* \* \* \* \*